(12) United States Patent
Jolie et al.

(10) Patent No.: US 12,344,831 B2
(45) Date of Patent: Jul. 1, 2025

(54) INCUBATOR, SYSTEM, AND METHOD

(71) Applicant: EPPENDORF SE, Hamburg (DE)

(72) Inventors: Christoph Jolie, Hamburg (DE);
Benjamin Paulsen, Hamburg (DE);
Wolf Lukas Hellweg, Hamburg (DE)

(73) Assignee: EPPENDORF SE, Hamburg (DE)

(*) Notice: Subject to any disclaimer, the term of this patent is extended or adjusted under 35 U.S.C. 154(b) by 150 days.

(21) Appl. No.: 18/262,158

(22) PCT Filed: Jan. 27, 2022

(86) PCT No.: PCT/EP2022/051878
§ 371 (c)(1),
(2) Date: Jul. 19, 2023

(87) PCT Pub. No.: WO2022/162056
PCT Pub. Date: Aug. 4, 2022

(65) Prior Publication Data
US 2024/0076602 A1    Mar. 7, 2024

(30) Foreign Application Priority Data
Jan. 27, 2021   (EP) .................... 21153820

(51) Int. Cl.
*C12M 1/00* (2006.01)
*C12M 1/36* (2006.01)
(Continued)

(52) U.S. Cl.
CPC ............ *C12M 41/14* (2013.01); *C12M 41/48* (2013.01); *G06T 7/248* (2017.01); *G06V 20/41* (2022.01); *G06V 20/52* (2022.01); *G06V 20/695* (2022.01); *G06V 20/698* (2022.01); *G06V 40/172* (2022.01); *H04N 7/183* (2013.01);
(Continued)

(58) Field of Classification Search
CPC ....... C12M 41/14; C12M 41/48; G06T 7/248; G06T 2207/10016; G06T 2207/30004; G06T 2207/30201; G06V 20/41; G06V 20/52; G06V 20/695; G06V 20/698; G06V 40/172; H04N 7/183
See application file for complete search history.

(56) References Cited

U.S. PATENT DOCUMENTS

| | | | |
|---|---|---|---|
| 2004/0147012 A1* | 7/2004 | Yokoi | C12M 23/48 |
| | | | 435/303.1 |
| 2016/0066565 A1* | 3/2016 | Reguzzoni | A01N 1/144 |
| | | | 435/39 |
| 2020/0172852 A1* | 6/2020 | Cannon | C12M 41/48 |

FOREIGN PATENT DOCUMENTS

| | | | |
|---|---|---|---|
| CN | 203419930 U | 2/2014 | |
| DE | 202014102506 U1 * | 8/2014 | C12M 41/14 |

(Continued)

OTHER PUBLICATIONS

International Search Report and Written Opinion dated May 19, 2022 issued in international patent application No. PCT/EP2022/051878.

(Continued)

*Primary Examiner* — Sath V Perungavoor
*Assistant Examiner* — Tyler B Edwards
(74) *Attorney, Agent, or Firm* — Dorsey & Whitney LLP

(57) ABSTRACT

The invention relates to a live cell culture incubator, a method of working with an incubator, and a system comprising an incubator in which an object tracking system is implemented.

17 Claims, 10 Drawing Sheets

(51) Int. Cl.
*G06T 7/246* (2017.01)
*G06V 20/40* (2022.01)
*G06V 20/52* (2022.01)
*G06V 20/69* (2022.01)
*G06V 40/16* (2022.01)
*H04N 7/18* (2006.01)

(52) U.S. Cl.
CPC .............. *G06T 2207/10016* (2013.01); *G06T 2207/30004* (2013.01); *G06T 2207/30201* (2013.01)

(56) References Cited

FOREIGN PATENT DOCUMENTS

| | | |
|---|---|---|
| EP | 1916296 A1 | 4/2008 |
| EP | 2028264 A1 | 2/2009 |
| EP | 3404090 A1 | 11/2018 |
| EP | 3539660 A1 | 9/2019 |

OTHER PUBLICATIONS

European Search Report dated Jul. 7, 2021 issued in European patent application No. 21153820.2.

\* cited by examiner

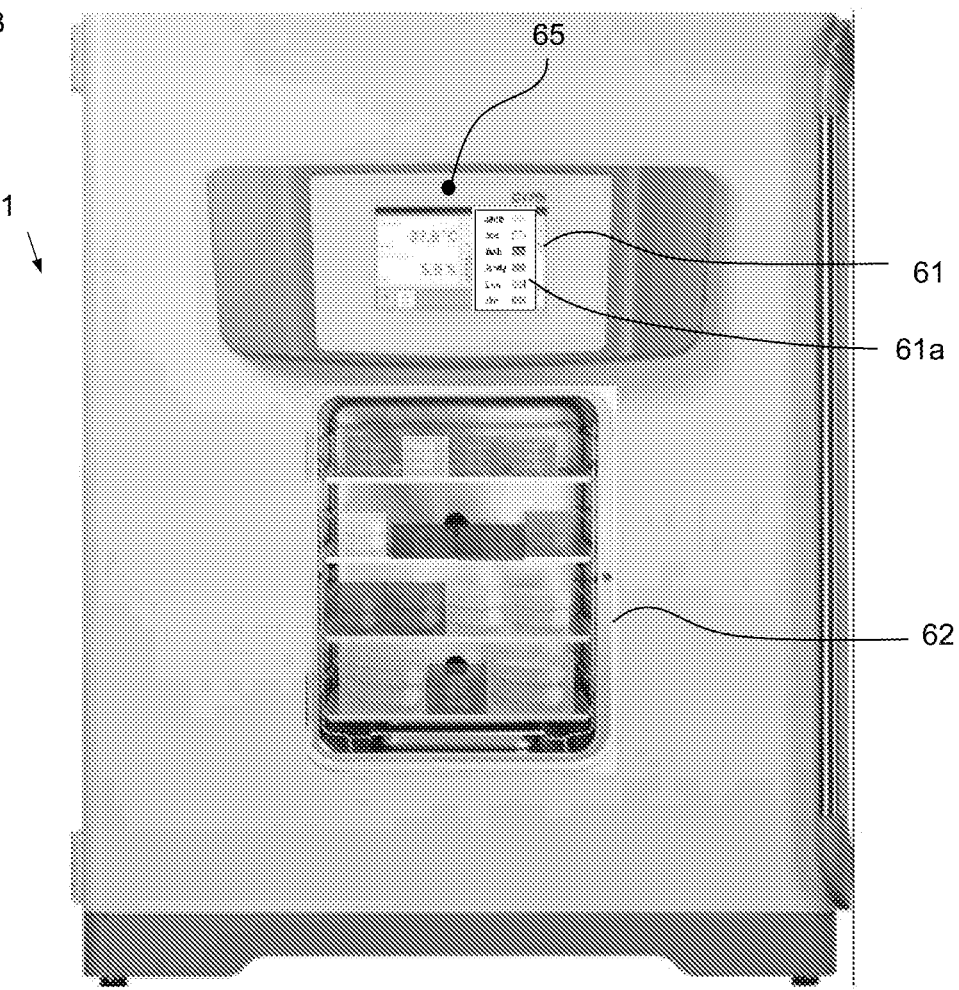
Fig. 3
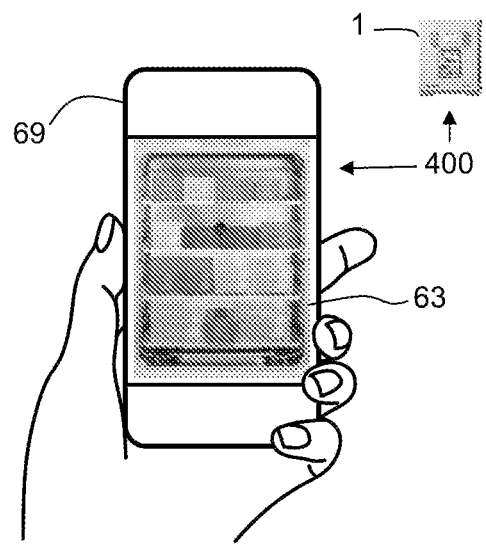
Fig. 4a
Fig. 4b

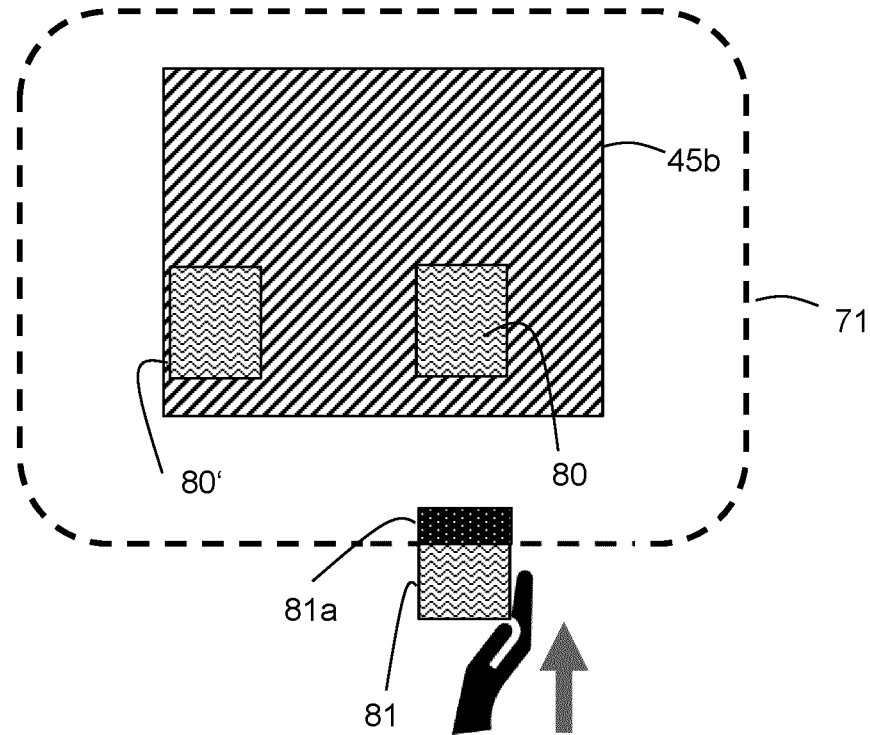
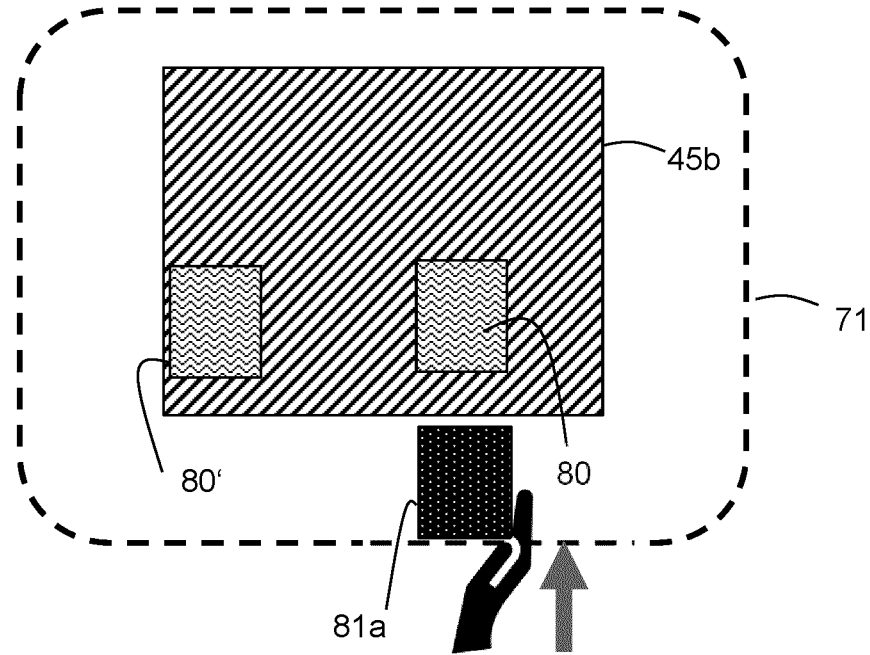

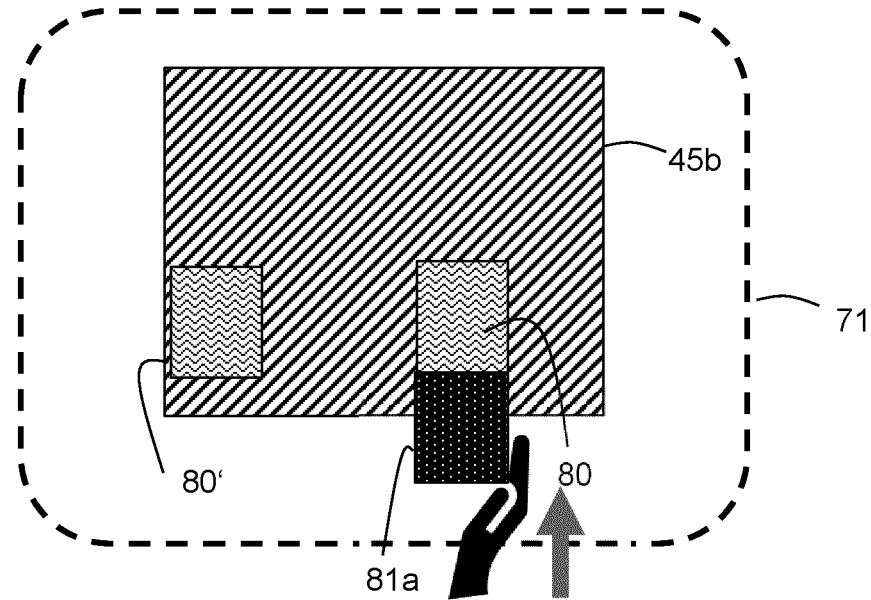
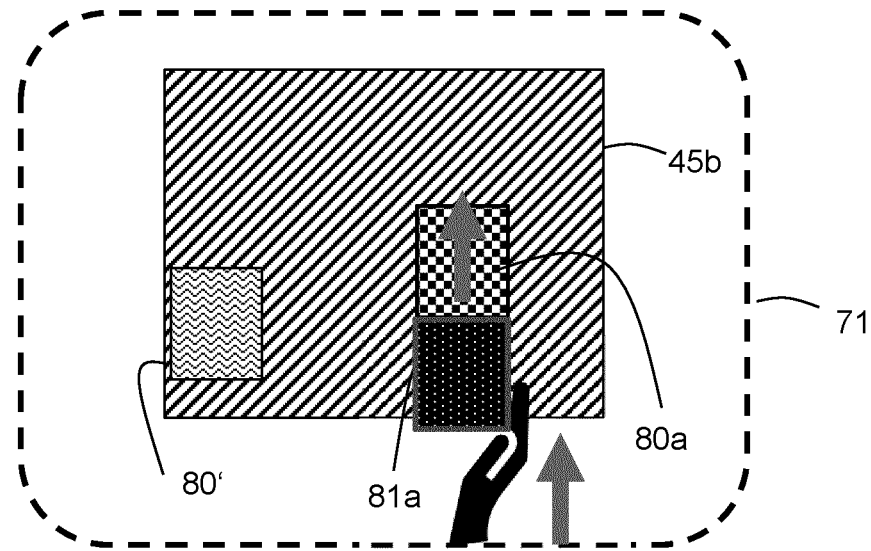

INCUBATOR, SYSTEM, AND METHOD

This patent application is a U.S. National Stage filing under 35 U.S.C. 371 of International Patent Application No. PCT/EP2022/051878, titled "INCUBATOR, SYSTEM, AND METHOD," filed Jan. 27, 2022, which claims priority to European Patent Application No. 21153820.2, filed Jan. 27, 2021, each of which is incorporated herein by reference in its entirety.

The invention relates to a live cell culture incubator, a method of working with an incubator, and a system comprising an incubator.

The invention relates to an incubator for the monitored growth of biological cells. The invention also relates to a system and method for the monitored growth of biological cells.

Such incubators are used in biological and medical laboratories to maintain cells in cell culture under controlled environmental conditions, thus enabling the growth of live cells in vitro. For this purpose, the temperature and gas composition or humidity of the atmosphere inside an incubator chamber isolated from the environment are maintained at the desired values by the incubator's apparatus. Eukaryotic cells require $CO_2$ incubators. The atmosphere is formed by air with a certain $CO_2$ and $O_2$ content and a certain humidity, a suitable temperature is often 37° C.

Cell growth is particularly critically dependent on the constancy of atmospheric conditions in the incubator. Disturbances of the incubator atmosphere can have a negative effect on the growth of the cells. In an "ideally" equipped laboratory, each individual user would be provided with a separately accessible incubation chamber for each sample to be incubated. However, this is not realistic for reasons of cost efficiency. In laboratory practice, it is common for a single incubator (or a few incubators) with a single incubation chamber and one or more storage areas on one or more storage plates in the incubation chamber to be provided for use by multiple users. The frequency of opening the chamber door of the incubator and thus interfering with the controlled atmosphere of the incubator scales with the number of users and, moreover, with the number of samples incubated there. The intensity of the interference also depends on the duration of the door opening. The more time a user needs to access the interior space of the incubator chamber, the longer the door remains open. There are various incubator usage scenarios that may require increased access time due to complications:

Scenario A) Setting New Objects in the Incubator.

When a user places one or more objects, in particular cell culture containers, into the incubator for the first time, he needs a free storage space in a storage area. If no free storage space is available due to disordered storage, the user needs time to create this storage space; the more carefully he moves or rearranges objects already present in the incubator (inventory objects), possibly even documenting this in writing, the more time-consuming the process becomes. If it turns out that there is no longer sufficient storage space available in the incubator chamber, the user repeats his procedure for a possibly existing further compartment of the incubator chamber or for a replacement incubator of the laboratory. This extends the period of the condition of an open incubator door, i.e. the duration of exposure of the chamber interior space to the environment (exposure duration).

Scenario B) Testing Cell Cultures

If a user checks the cell cultures he has previously placed in the incubator, e.g. to assess the quality of the cell medium or the state of growth, the user will first look for the cell culture container in question in the incubator. He may not remember the storage location he has chosen, or other users may have changed this storage location—both of which extend the exposure time, i.e. the opening time of the incubator and the incoming atmosphere losses. The more carefully the user moves or rearranges inventory objects, the more time-consuming the search process becomes.

Scenario C) Removing the Objects from the Incubator

In this case, too, the user must first search for the corresponding object. The time-delaying factors mentioned in b) apply.

Moreover, the more frequently an incubator is opened, the higher the risk of contamination of the interior space. There are also cases, for example in forensics or reproductive medicine, where the value of a single sample, especially the cell(s) contained in a cell culture vessel, is much higher than, for example, the value of the entire incubator, so that loss of the sample due to contamination must be avoided at all costs. In any case, the frequency of contamination increases the risk of lost work, increased costs, and an additional maintenance effort. Following contamination of an incubator, the chamber must be cleaned and sterilized before the incubator can be used further. During this time, unless a replacement incubator is available, work with cell cultures is interrupted.

In laboratories, therefore, there is a fundamental need to keep the time period during which the incubator door is open as short as possible and also to keep the frequency of opening the incubator chamber as low as possible.

The task underlying the present invention is to provide an incubator which can be used efficiently and which, in particular, makes it possible to keep the exposure period, i.e. the period of the state of an open incubator door, and thus the period of exposure of the interior space of the incubator chamber to the environment of the incubator low.

The invention solves this problem by the incubator according to claim 1, the system according to claim 12, and the method according to claim 14. Preferred embodiments are in particular objects of the dependent claims.

The incubator according to the invention for incubating live cell cultures, comprises:
- an incubator chamber for receiving objects, in particular cell culture containers, which comprises a closable chamber opening for loading and unloading the objects and at least one storage area for storing the objects,
- an image-based object tracking system for tracking position changes of at least one object introduced into the incubator chamber starting from its start position in a start image of a storage area to its end position in an end image of the storage area by means of video data, wherein the object tracking system,
- comprises at least one data processing device, a data memory and at least one camera which is configured to monitor an interior space of the incubator chamber, in particular a storage area, and to provide the start image, the end image and the video data,
- wherein the data processing device is programmed to do so,
  - assign identification data to the at least one object introduced into the interior space, (this step is also called object registration)
  - determine the start position of the at least one object from the start image of the storage area,
  - determine the position changes of the at least one object between the start position and an end position by evaluating the video data, determine the final position of the at least one object in the final image of the storage area, and to store the end position of the at least one object in the storage area in dependence on the identification data as ID position data in the data memory.

The incubator according to the invention "knows" the object "registered" when it is placed in the incubator by means of an internal system name, namely the identification data assigned to this object (can be an identification number, or another identification code consisting of any characters or information). Based on the position tracking, the incubator knows the final position of the object after each position change, which is generated, for example, when another user moves the object in the incubator at a later time. The incubator "remembers" the final position of the object, and preferably other objects, or any other object in the incubator chamber. The aim of object tracking is to be able to unambiguously assign to the object located at the start position, after its position changes, i.e. its movement in the camera field of view, its end position at which the position changes are zero and the movement of the object has ended. It is not primarily relevant to be able to precisely describe the entire motion path of the object moved by the position changes. However, this may be provided in a preferred embodiment of the invention.

Image-processing object tracking techniques are well known, for example when used in drones or driver assistance systems for vehicle or person tracking. Object tracking is based on image processing or image analysis of video image data. Such object tracking methods can be implemented with relatively simple means such as suitable cameras and image processing algorithms. The theoretical basics and their use for the practical realization of object tracking techniques are well known, especially the realization of "single object tracking" and "multiple object tracking" (e.g.: "Fundamentals of Object Tracking," S. Challa et al, Cambridge University Press, 2011). Immediately usable image processing algorithms for object tracking are also freely available (OpenCV.org) and well documented. OpenCV (English abbreviation for Open Computer Vision) is a free program library (BSD license) of algorithms for image processing and computer vision. The OpenCV program library also includes functions for tracking multiple objects in real time. The application of object tracking in incubators has not been published yet and represents an innovation.

A typical mode of operation of image-processing object tracking, which is preferably also used in the object tracking system according to the present invention, is based on the evaluation of the temporal sequence of images. A typical object tracking program code uses a "bounding box" as output format to identify an object in an image, to define its collision boundaries and, in particular, to localize it. In digital image processing, the "bounding box" refers to the coordinates of the rectangular frame that encloses most or all of an object shown in the digital image. The use of bounding boxes in object tracking makes it more efficient, since image evaluation by means of such a numerical tool requires fewer computational steps and thus less computational power, especially in comparison with algorithms for outline detection of objects. In addition, the corresponding algorithms can be executed efficiently and cost-effectively using specialized graphics processing units (GPUs). Suitable programming interfaces (APIs) for object tracking using bounding boxes are available in the OpenCV program library under the names BOOSTING, CSRT, GOTURN, KCF, MEDIANFLOW, MOSSE, MIL, TLD. Accordingly, program libraries ("MultiTracker") are available in OpenCV for simultaneous tracking of multiple objects ("multiple object tracking"). Alternatively, deep learning algorithms for multi-object tracking (MOT) according to the "tracking-by-detection" principle are known.

However, it is also possible and preferred that for object tracking a determination of the contour of the object to be tracked in the image is performed, and in particular the separation of object (foreground) and background by background subtraction.

On the one hand, the performance potential of an object tracking system is based on a reliable automatic identification of an object in the incubator in different typical usage scenarios of an incubator, which are described below. On the other hand, the approach is efficient because no special adaptations are required on the part of the object. In particular, the object does not need to include passive (code, labeling) or active (e.g., a transmitter) identification aids. Rather, the usual objects (cell culture containers, devices, etc.) can be used with the incubator, in particular regardless of manufacturer and external appearance. In particular, the incubator according to the invention is able to distinguish objects with completely identical appearance by tracking.

Possible scenarios when changing occupancy in an incubator include:

I. Setting new objects

II. Removal of objects

III. Door is opened and objects are only moved without removing or resetting one.

Subconditions:

i) Object(s) are moved ii) Object(s) are not moved iii) Several objects are set/taken out (sequence).

Assumption: all cell culture containers look the same externally. The question underlying the development of the invention was, in particular, which image-based methods could be considered, and in particular whether still images are sufficient to enable object identification in common usage scenarios of an incubator.

It is first assumed for scenario I. (new object is to be inserted into the incubator chamber) that there is a current still image of the storage area in the incubator chamber taken by a camera placed in the incubator before the incubator door is opened, which does not yet show the new object.

If the new object is placed in the incubator chamber without moving the stock objects (objects already placed and located in the storage area) (case I.ii), the new object can be identified (unambiguously without any problems) via the next still image (after closing the incubator door). Object tracking is not necessary for case I.ii). The same applies to II.ii): in case of removal of an object, its identification is unambiguously possible from the evaluation of the still images before and after door opening.

If the new object is set and inventory objects are moved in the process (case I.i)), the new object cannot be uniquely identified via the next still image. Location information about the already registered inventory objects is lost. The same applies to the removal of an object and the resulting movement of the inventory objects (case II.i)). For moving (condition i)) the concept of object tracking comes into play.

If several objects (case iii)) are adjusted under condition i), i.e. without moving the stock objects, the new objects can be easily identified by before-after still images, but the information about the order of adjustment is lost. If you want to get this information, you need the object tracking. The same applies to the case of removing several objects in case i)+iii). However, the order of setting is rarely crucial. In particular, for incubation durations of e.g. 48 h, the second does not matter. In particular, however, if the object assignment is to be resolved for the case that objects of several persons are placed in the incubator chamber one after the other with the incubator door open, or if the moving of objects from one shelf of the incubator chamber to another incubator chamber is to be tracked, the recording of the sequence or the recording of the temporal course of the moving of objects may be desired. For "basic tracking" where users follow certain rules of operation of the incubator, sequence capture may not be required.

Since moving inventory objects is the rule rather than the exception in the operation of an incubator, an evaluation of the before-and-after still images of the storage area is not sufficient in this case.

One question in particular when developing an object tracking system in an incubator is: When is an object identified, i.e., at what time or event is identification data assigned to the object? In most application scenarios (except for a case such as iii)+i), where it may still be important to record the order in which objects are set), it is sufficient to collect this identification data when the new objects have been set and any inventory objects have been moved in the process. This is because moving the already registered inventory objects is done under the object tracking measure. In the next freeze frame, i.e. especially when the incubator door is closed, the registration of the new objects can then take place on the basis of the freeze frame. If, however, the registration of the sequence is desired, at the moment when an object enters the field of view of the camera for the first time, i.e. when it appears for the first time in an image recorded by the camera (a start image, which in this case is a video image), this is registered, i.e. an ID number is assigned to the object, and this object is tracked to its end position, the possible moving of stock objects or their removal is preferably also tracked in the process.

In another practical scenario, the storage area (or several storage areas) is assumed to be occupied by one or more objects (stock objects), which are registered on the basis of an initial start image (in this case, for example, a still image). Only the eventual movement of these inventory objects must be tracked here. The movement of newly set objects does not have to be tracked here during the setting process, because their registration can take place again in the next still image. The corresponding presence of these new objects in the video data can thus be ignored. In this scenario, the information about the sequence of setting several objects during a door opening is lost, but this information is also not absolutely necessary.

Accordingly, the invention proposes to implement object tracking to ensure the correct localization of objects, as needed, in various or all situations.

The data processing device is programmed in particular to assign identification data to the at least one object introduced into the interior space. This means in particular that a new object is detected in the image data (still images or video data) of the camera. In particular, a new object is detected when it is moved into the camera's field of view from the outside. When the object is detected, identification data can be assigned to it (registration) on the one hand, and position data on the other. The position data, in particular the start and end position of an object, are determined in particular with reference to an internal coordinate system, which is also used to define the position of the at least one storage area and thus also the position of the at least one object with respect to the at least one storage area. This position information is of particular importance if the position of the at least one object in the at least one storage area or in the incubator chamber is to be graphically illustrated to the user on a display.

These identification data can be predetermined, randomly generated, or given by a user, especially as long as they are suitable to uniquely distinguish the newly placed object in the incubator chamber from the identification data of the other stock objects. The identification data may also be predetermined and merely selected. The latter case is covered by the term "assign" as well as the re-creation of the identification data.

In particular, the data processing device is programmed to determine the start position of the at least one object from the start image of the storage area. The start image is preferably a still image taken in a still image mode of the camera. It may also be a still image obtained from video data, in particular a video frame. The data processing device is programmed in particular to determine an enveloping or marking line figure, preferably rectangle, or an enveloping or marking body, or in particular a bounding box of the object, or an outer contour of the object, in the start image and, in particular, to define the object as the image area enclosed or marked by the enveloping or marking line figure, in particular by the bounding box or an outer contour.

The data processing device is programmed in particular to determine the changes in position of the at least one object by evaluating the video data. The data processing device is programmed in particular to track the movement of the object defined in the start image by means of the bounding box. In particular, the data processing device is programmed to detect the movement of the image area defined in the start image by means of the bounding box and containing the object by determining the changes in position of this image area from frame to frame. In particular, tracking of the bounding box can be used to determine the image area changing position due to the object movement. Video data contains in particular information, by means of which the single frames characterizing the video ("frames", which are represented in the case of the representation of the video with certain number per time thus "framerate") can be reconstructed. In the case of uncompressed video data, the latter may also contain the complete sequence of frame data, where a "set" of frame data represents one frame at a time. In the case of compressed image data, temporal changes of pixels of the camera image may also/only be captured.

The data processing device is programmed in particular to determine the start position of the object in the storage area from the start image. The start position can be determined in particular by the fact that the object, which was previously motionless in a first frame of an image series, shows a change in position of the object in the subsequent frame. The first frame in which the object shows a change in position compared to the previous frames can be defined as the start frame. Since the motion of the object starts at a time T1 and ends at a time T2, an image (still image or video image, also an image obtained from superposed images) acquired before the time T1 can be used as the start image from which the start position of the at least one object is determined.

The data processing device is programmed in particular to determine the final position of the at least one object in the final image of the storage area from the position changes. The end position can be determined in particular by the fact that no more position changes of the object are determined from frame to frame. The first frame in which the object no longer has any change in position compared to the previous frames can be defined as the final image. Since the motion of the object starts at a time T1 and ends at a time T2, an image (still image or video image, also an image obtained from super-positioned images) acquired from time T2 onwards can be used as the final image from which the final position of the at least one object is determined. The end position can be determined in particular by the time at which a closing of the incubator door is detected by means of the door sensor. In particular, the end position can be determined by the fact that an arm or hand of the user leading into the image area is no longer detected. For example, an image can be evaluated to determine whether a section, e.g., in the form of a strip, located in the image border area corresponds to a reference state in which a reference section of the incubator chamber or incubator is completely visible. If this is not the case, it can be concluded that a user is still handling inside the incubator and the object or multiple objects are still being moved, so that in particular the video image acquisition and analysis is to be continued. The end position of the object can be understood as the position where the object no longer shows a change in position after previous changes in position, thus can be determined by the end of the movement of the object. Alternatively or additionally, the end position of the object may be defined to be the position that the object holds when the closing of an incubator door is detected by means of a door sensor. As a result, the end position will be the same in most cases.

The data processing device is preferably programmed to start capturing the start image and/or video data using the camera when a sensor detects activity occurring at the incubator. The sensor may be a motion sensor that detects motion in a detection area located outside the incubator. The sensor may be a touch sensor that detects a touch performed by a user on the incubator, such as a door handle of the incubator. The sensor may be a door opening sensor that detects an opening of an incubator door, in particular an exterior door of the incubator. The sensor may be an exterior camera of the incubator that uses image analysis to detect motion and/or a person in the camera's field of view. The sensor may be a proximity sensor that detects, for example by detecting a change in an electric field, the approach of a person to the incubator. An activity occurring at the incubator can also be a code entry at a door lock, which is preferably detectable by the data processing device even without a sensor.

The data processing device is preferably programmed to start the acquisition of the final image and/or stop the acquisition of video data when a sensor detects an activity occurring at the incubator. The sensor may be a door opening sensor, in particular detecting a closing of an incubator door, in particular an exterior door of the incubator. The sensor may be an outside camera of the incubator that uses image analysis to detect the termination of a movement and/or the disappearance of a person in the camera's field of view. The sensor may be a proximity sensor that detects, for example by detecting the change in an electric field, the removal of a person from the incubator.

The data processing device is programmed in particular to start the acquisition of video data by means of the camera initiated by the opening of an incubator door detected by means of a door sensor. Alternatively or additionally, an initial event sensor, in particular a motion sensor, or proximity sensor, or optical sensor/receiver (e.g. light barrier), or microphone, or acceleration sensor in the incubator door, may be arranged in the incubator, by means of which the approach of an object to the incubator chamber or another initial event can be detected; the data processing device may be programmed to start the acquisition of video data based on the data from such a sensor. The data processing device may be programmed to start searching for a new object in the images (frames) available by means of the video data or the still image when the video data is available and/or when a still image is available. Alternatively, video data acquisition can start as soon as a user is identified at the incubator, or at some other predetermined event. Permanent video data acquisition is also possible. In particular, the data processing device is programmed to terminate the acquisition of video image data with the acquisition of the final image or the registration of the absence of a hand/arm in the camera field of view, or based on the results of one of the mentioned sensors (door sensor, motion sensor, etc.).

In particular, the data processing device is programmed to store the final position of the at least one object in the storage area as ID position data in the data memory depending on the identification data of the at least one object. With this step, the incubator "knows" "the object" and its position. Together with other data, it can now output this data to a user, in particular show it on a display of the incubator. Together with data about the owner (the user who placed the object in the incubator chamber) of the object or a user of the object (e.g. a user who moved an inventory object of another user), the incubator can store and collect these data sets depending on the identification data of the object. The identification data on the basis of which the position changes were detected need not be identical to the identification data stored as ID position data; what is relevant is that the stored identification data is suitable for uniquely distinguishing the at least one object from other objects or inventory objects. The ID code can therefore theoretically change during image processing.

The assignment of an owner to an object may be accomplished in a variety of ways. Preferably, the data processing device is programmed to register or identify the user placing the object in the incubator, assign a user identification code to this user, and store user-related ID position data of the object. For a user registration, a biometrics recognition, in particular facial recognition, of the user can be performed, in particular by means of an outdoor camera, a retina scanner or a fingerprint sensor of the incubator. The corresponding registered biometrics recognition data, in particular facial recognition data of the user can be stored in the data storage device of the incubator, or in an external data storage device. The user may be identified based on a comparison of captured biometrics recognition data with previously registered biometrics recognition data. As an alternative to biometrics recognition, a user may also be enabled to enter user identification data via a user interface device before, during, or after performing object registration or determining the final position of a tracked object. The user interface device may be a keyboard, a touch screen, and may be part of the incubator or an external device.

An advantage of object tracking is that it can be performed without knowledge of individual or class characteristics of the object to be tracked. However, it can also be combined with methods for object detection (and redetection) and/or object class detection or class redetection.

An object recognition can be designed in particular as object individual recognition and/or as object class recognition. The theoretical principles and their implementation for practical application in object recognition technologies are well known (e.g.: "Deep Learning in Object Detection and Recognition," X. Jiang et al, Springer Singapore, 2019). Algorithms for object recognition in images are widely known and available, e.g., as part of OpenCV (for example, OpenCV 3.3, deep neural network (dnn) module).

Individual object recognition is based on the recognition of object-specific features (individual object characteristics), which can be used to recognize the individual object and distinguish it from other individual objects. For example, a cell culture container, e.g. a disposable product, can have subsequently applied individual features, e.g. a barcode or QR code. However, it can also be identifiable by any features that allow it to be distinguished: e.g., a label, a different content, a micro-scratch pattern on the container surface, etc . . . .

Object class recognition relies on knowledge of object class features that are matched during object inspection to assign a class to the object. For example, object class recognition can be used to detect whether an object is a certain type of cell culture flask, a certain type of Petri dish, or a certain type of microtiter plate, possibly taking into account other class features, e.g., manufacturer, year of manufacture, design, etc., as well.

The incubator preferably has an object detection system. The object tracking system is preferably additionally set up for object recognition.

In the case of object individual recognition, a data processing device of the object recognition system or the object tracking system is preferably programmed a) to recognize individual features of at least one object in a still image, the start image, the video data and/or the end image, and b) to store these individual features of the object in the form of object individual data, in particular as a function of identification data. Preferably, the data processing device is programmed to extract object individual characteristics of the at least one object from the start image, the video data and/or the end image, to compare the object individual characteristics with an object individual database and, if the object individual characteristics in the object individual database are associated with an object individual identifier: identify the object individual identifier of the at least one object; or, if the object individual characteristics in the object individual database are not linked to an object individual identifier: assign an object individual identifier to the at least one object and store it in the object individual database, and/or assign the recognized object individual identifier to the ID position data of the at least one object and store it as individual-related ID position data. An object individual identifier is preferably different from its identification data; however, the object individual identifier can also preferably be the same as its identification data.

In the case of object class recognition, a data processing device of the object recognition system or the object tracking system is preferably programmed to a) recognize class features of at least one object in a still image, the start image, the video data and/or the end image, and b) store these class features of the object in the form of object class data, in particular as a function of identification data. Preferably, the data processing device is programmed to recognize object class features of the at least one object in a still image, the start image, the video data and/or the end image, to match the object class features with an object class database (which in particular contains preknown correlations between the object class and object class features) and to recognize the object class of the at least one object, and in particular to assign the recognized object class as object class data to the ID position data of the at least one object and in particular to store it as class-related ID position data.

Preferably, the incubator comprises a user identification device by means of which a user using the incubator is identifiable in terms of user identification data. Preferably, a data processing device of the incubator is programmed to identify a user using the incubator by means of the user identification device and to assign user identification data thereto and to store identification data and/or ID position data in dependence on the user identification data as user-related identification data and/or user-related ID position data in the data memory.

Preferably, the user identification device comprises an external camera, and preferably the user identification device is arranged and/or the data processing device is programmed to perform a facial recognition by means of the external camera, by means of which the user is identified. Preferably, a user database is provided, which is stored on a data storage device, which may be part of the incubator, the user identification device or the object tracking system, or which may be in a data exchange connection with the user identification device or the data processing device, e.g. via an intranet or the internet. Algorithms for face recognition in images are generally known and available, e.g. as part of OpenCV ("FaceRecognizer class").

The user database may contain a correlation of user identification data and user feature data so that the user or the user's user identification code (user identification data) can be determined based on the determined or read user feature data. The user feature data may include information about users' facial features, or other biometric data, such as fingerprint data or voice recognition data. The user database may include a correlation of user identification data and user identifiers, where the user identifier may be a personal identification code of the user, e.g., a multi-digit string of characters that a user can use to identify himself or herself when entered at a keyboard of the user interface device.

In particular, the external camera can be arranged on, above or next to an incubator door, in particular an external door on the incubator, or attached to it. Preferably, the external camera is an integral part of the incubator or the incubator door. However, it can also be connected to the user identification device or the data processing device via a signal connection, in particular via a data exchange connection, which can be wired or wireless. For example, it is possible to connect the external camera to the incubator or its user identification device or the data processing device via a flexible cable, so that the camera can be freely placed on the incubator by the user.

Preferably, the user identification device comprises a user interface device by means of which user identity data can be read. The user interface device may include a keyboard, and/or a touch screen, and or a microphone for voice input or for implementing user identification by means of voice recognition. The user interface device may be arranged to exchange data with an external data processing device (hereinafter also referred to as "external device"). The external device may be a PC, a smartphone, a tablet computer, or another portable computer with a user interface.

The external device may include means to identify and/or authenticate a user. In particular, currently available smartphones include various means for user authentication, especially facial recognition. The external device preferably has software, e.g., an app, programmed to identify and/or authenticate a user, and in particular to send the result of this process to the user identification device of the incubator via the user interface device. Since an external device also often has its own camera, by means of which facial recognition may be implemented, or a fingerprint sensor, or other hardware for user identification and authentication, the corresponding hardware components are dispensable in the case of connection of the incubator to the external device on the incubator.

The user identification device of the incubator may be programmed as part of a control software of the incubator. The incubator preferably has a control device, which may in particular have a data processing device, which may in particular be programmed to include all or some functions of the user identification device, in particular to control the exchange of data with the external device.

Preferably, the user identification device comprises a user interface device by means of which user identity data can be selected. For this purpose, in particular the user identification device can have a display or a touch screen by means of which a list of possible users can be displayed, e.g. by specifying a name or image of the user. Input means can then be provided, e.g. keys, a keyboard, touchpad, the touch screen, via which the user can make the selection from the list.

The user identification device may be programmed to perform user authentication by password-protecting said reading of user identity data or said selection from the list, so that the user is not considered identified until authentication is successful.

Preferably, the user identification device comprises a reader for reading a code identifying the user, the reader being in particular an RFID reader, a barcode reader, or a QR code reader.

The user identification device or a/their data processing device can be programmed to unlock and/or lock a locked incubator door depending on the user identification, in particular to unlock a locked incubator door if the user has been successfully identified. In this case, this means that the user is also authorized to access the incubator. However, there may also be an additional access right list that the incubator uses to decide whether an identified user has the access right or, if applicable, what type of access right the identified user has. For example, the access right may be limited to certain times, especially days of the week, times of the day, or authorization time periods. If the incubator has multiple incubator doors, the access right may provide that the user has the access right only for a predetermined selection of those incubator doors.

Preferably, the incubator has exactly one—or even several—incubator door(s) for closing the chamber opening. When closed, the incubator door forms in particular a part of the incubator housing, which serves as a thermal insulator of the incubator chamber of the incubator. The incubator door may have a user interface device on its exterior, in particular a display. A data processing device of the incubator or the user interface device may be programmed to display an image of the at least one storage area of the incubator taken by the camera of the incubator.

Preferably, the incubator comprises a door sensor for detecting the opening or closing of the incubator door. Preferably, the data processing device is programmed to start the monitoring of the interior space of the incubator, in particular the generation of the video data and/or still image data, depending on the detection of a door opening of the incubator, in particular by means of a door sensor, alternatively also by means of a motion sensor or proximity detector;

preferably, the data processing device is programmed to start the monitoring of the interior space of the incubator, in particular the generation of the video data and/or still image data, in particular in response to the detection of a door opening by a user identified by means of a user identification device;

preferably, the data processing device is programmed to terminate the monitoring of the interior space of the incubator, in particular the generation of the video data, in response to the detection of a door closure or in response to the measurement of one of said sensors of the incubator;

in particular, the data processing device is programmed to determine, by means of the information from the user identification device and the object tracking device, by which user which object was moved in the interior space, and to store the user identification data of this user together with the object identification data of this object in the data memory.

Preferably, the data processing device is programmed to determine the movement path of the at least one object within the incubator chamber from the start image, the video data and/or the end image and to store it in the form of movement history data in the data memory, in particular to store it in a time-dependent manner. Preferably, the data processing device is programmed to determine a movement history of the at least one object within the incubator chamber from the start image, the video data and/or the end image and to store it in the data memory in the form of movement history data, in particular to store it in a time-dependent manner, preferably with information about the number and/or times of the changes in the status of the door opening (open/closed) of the incubator door determined by means of a door sensor. The movement path preferably contains stored position data of the object, wherein these position data mark the movement path of the object, in particular between a start image and an end image, in particular between a—in particular unmoved or also moved—start position of the object and a—in particular un-movedend position. The motion history data preferably contains time-dependent stored position data or motion paths, preferably within at least one time period or during the entire stay of this object in the incubator. Motion history data may also include information about the user initiating the position change in the form of user identification data. This is particularly advantageous for objects containing valuable specimens.

Preferably, the incubator comprises a display (=a screen). The screen is preferably an integral part of the incubator, in particular of the incubator door. However, it can also be arranged remotely from the incubator and can, in particular, be part of an external device that can be in a data exchange connection with the data processing device of the incubator.

Preferably, the data processing device is programmed to display a graphical rendering of the interior space of the incubator chamber, in particular the at least one storage area, on the display screen. The graphical rendering may include a photograph of the storage area, which may display one or more inventory objects of the incubator. In particular, the storage area may be a shelf in the incubator or a predetermined section thereof. The photograph may show an image taken with the camera, which may be post-processed. Preferably, this post-processing involves straightening an image taken by the camera in a distorted manner. Algorithms for such post-processing are generally known and freely available (for example: OpenCV, "Omnidirectional Camera Calibration"). The distortion can be especially optical and can be caused by the use of a wide-angle or fisheye camera.

In particular, the graphical rendering may be an abstracted representation of an image or portion of an image captured by the camera. For example, the graphical rendering may be an abstracted stock area shown from a bird's eye view (or other perspective), in particular the graphical representation of a rectangle or the perspective representation of a cuboid. The inventory objects may also be represented in abstracted form, e.g., as rectangular or cuboid graphic image objects. The goal of such a representation is, in particular, to inform the user of the location of the object(s) in the incubator or storage area. This allows the user to quickly access the desired object(s) and minimizes the time the incubator door is open. In the case where differentiation between individual objects contained in a stack of objects is to be enabled, a graphical rendering from a perspective different from the bird's eye view is useful, for example from a lateral perspective, in order to be able to graphically highlight individual objects of a stack.

Preferably, the data processing device is programmed to graphically display where the object identified by the object position data, i.e., the ID position data, is located in the storage area or in the interior space of the incubator chamber, or to graphically display where all objects located in the interior space are located.

Preferably, the data processing device is programmed to graphically highlight one or more objects in the display in response to at least one condition parameter. The condition parameter may denote user identification data:

Preferably, the data processing device is programmed to graphically highlight, in dependence on user identification data of a user (individual user, a user group, or several users), one or more objects that are assigned as property to the user, namely, for example, by the user-related ID position data containing the user identification data of this user. The owner is the person who has taken care of the object and—in most cases himself or with the help of an assistant—has placed it into the incubator chamber. Preferably, the data processing device is programmed to determine, based on predetermined user identification data, where the objects assigned to this user identification data by means of the user-related object position data are positioned and, in particular, to highlight these objects graphically.

The condition parameter can also contain information about a time duration or a point in time, e.g. the time duration with which an object was already arranged in the incubator chamber. This allows a user to quickly get an overview of how long one or more objects have already been stored in the incubator chamber, possibly forgotten there by their owner. Or, depending on an event detected by a sensor of the incubator or depending on a schedule that may be stored in the incubator or an external device, the incubator can graphically highlight one or more objects that require the attention of the user or laboratory personnel.

Or the condition parameter may, in case of implementation of object class recognition, contain information about a particular object class. Thus, one or more objects of the same object class (or the object classes differing from it) can be graphically highlighted, for example, to highlight the location of all Petri dishes (and not: cell culture flasks) in the incubator interior space.

Or, in the case of implementing object individual recognition, the condition parameter may include information about a particular object individual. In this way, an object search based on individual features can be implemented, for example, by the incubator having means for inputting individual features, such as a barcode, QR code, individual label, or photo of the individual object. It can thus graphically highlight the individual object and make it easy to find.

Preferably, the data processing device is programmed to display on the screen a graphical representation of the interior space of the incubator chamber, in particular the at least one storage area, and in particular to graphically display or highlight the free storage space available in the incubator. For example, the storage area may be shown in an abstracted manner and a free storage position (or several available free storage positions) may be graphically highlighted by displaying the corresponding area in, for example, green or white, or a temporally changing (flashing), contrasting color to the background. In this way, the user does not have to spend time searching for a possible free storage location, or creating one by moving inventory objects.

Moreover, similar to the function of a parking attendant, the data processing device may be programmed to plan the occupancy of the interior space of the incubator chamber or of the at least one storage area and, in particular, to optimize the use of the available storage space in this way. To this end, the data processing device may be programmed to take into account predetermined distances between one or more inventory objects to an object to be newly inserted and, in particular, to suggest them to the user by displaying the free storage space accordingly highlighted as available and/or unavailable. According to these examples, the incubator may comprise a computer/software-implemented planning program for occupying the interior space of the incubator, which in particular takes into account the position of at least one object in the interior space (inventory object) and/or in particular the free available storage space, possibly also the times at which the at least one inventory object has been newly placed, or times in the future at which the placement of further objects in the incubator are planned. Such times may be known, in particular, if the incubator is connected to a laboratory information system (LIS) or other (laboratory) data exchange network. The incubator preferably has a timer, a clock, or a timer.

However, it is also possible and particularly preferred that the data processing device of the incubator (hereinafter: "first data processing device") controls the execution of a measurement of at least one measured value, in particular to measure a parameter (temperature, gas partial pressure) characterizing the atmosphere inside the incubator chamber. In this way, during the operation of the object tracking system, it can be taken into account by the first data processing device that the operation of electrical equipment inside the incubator chamber may lead to waste heat that heats the chamber atmosphere to an unacceptable extent. The control device of the incubator can therefore be set up in particular to control the operation of the electrical devices, in particular of the at least one camera within the incubator chamber, as a function of temperatures of the chamber atmosphere detected by means of temperature sensors. The control device of the incubator can in particular be configured to control the temperature control of the chamber atmosphere by means of the at least one temperature control device of the incubator and the operation of the electrical devices within the incubator chamber as a function of one another in order to compensate for the undesired heating of the chamber atmosphere.

It is possible and particularly preferred that a data processing device of the incubator is programmed to determine an occupancy state of the interior space of the incubator chamber, and/or is preferably programmed to perform one or more of the following steps, in particular to determine an occupancy state of the interior space of the incubator chamber as a function of the ID position data of the at least one object arranged in the interior space, determining an occupancy state of the interior space of the incubator chamber as a function of the class-related ID position data of the at least one object arranged in the interior space, determining an occupancy state of the interior space of the incubator chamber as a function of the individual-related ID position data of the at least one object arranged in the interior space.

An occupancy state of the interior space may be defined by information describing the volume occupied in the interior space by the at least one object, and/or describing the volume not occupied in the interior space by the at least one object, i.e. the free volume, and/or the storage area occupied by the at least one object on at least one storage area or on the total available storage area in the interior space of the incubator chamber, and/or the storage area not occupied by the at least one object, i.e. the free, storage area on at least one storage area or on the total available storage area in the interior space of the incubator chamber, wherein said information may be related to the total interior space volume or the total storage area, respectively, wherein said information may include, for example, the ratio of an unavailable (occupied) or a free (unoccupied) interior space volume to the total volume of the interior space, or wherein said information may include, for example, the ratio of an unavailable (occupied) or a free (unoccupied) storage area to the total storage area in the interior space.

Occupancy state data containing the information about the occupancy state can also contain the ID position data, class-related ID position data and/or individual-related ID position data. In this way, the specification of a spatial resolution of the occupancy is possible, i.e. the specification for the localization of the occupancy in the interior space, or a density distribution of the objects in the interior space.

It is possible and particularly preferred that a data processing device of the incubator is programmed to store information about the occupancy status of the incubator in the form of occupancy status data in a data memory, in particular to transfer it to an external data processing device, in particular a laboratory device, a PC, or a mobile computer, in particular a tablet computer or a smartphone. This information is stored in a retrievable manner, in particular retrievable by the user by means of a user interface device.

It is possible and particularly preferred that a data processing device of the incubator is programmed to display information about the occupancy status of the incubator on a screen of the incubator or of an external data processing device, in particular in dependence on occupancy status data that may be taken from a data memory. The external data processing device may be part of a laboratory instrument, PC, mobile computer, in particular a tablet computer or smartphone.

In test series based on embodiments of the present invention, it was found that the temporal temperature profile in the incubator chamber resulting from the temperature control after an opening of the incubator door depends on the occupancy state of the incubator chamber. If a larger volume of the chamber interior space is occupied by stock objects, there is a smaller free chamber interior space volume that results from the difference of the chamber interior space volume and the occupancy volume occupied by the objects. In this situation, temperature control designed to control the total interior space volume may produce different, undesirable results. Rapid overshooting may occur, which is undesirable, even though the recovery of the target temperature, e.g. 37° C., may be accelerated in the process, i.e. even though the recovery time may be shortened in the process. If several new objects with lower temperatures than the target temperature are reset, the recovery time may also be delayed, but the knowledge about colder, newly set objects can also be used to adjust the temperature control. Temperature control of the temperature inside the incubator chamber depends on control parameters.

Preferably, an electronic control device of the incubator is configured or programmed to operate at least one temperature control device of the incubator, which is arranged to control the temperature of the incubator chamber, with the electrical power $P_{temp}(t)$ during the temperature control as a function of the time t. The electronic control device of the incubator can be programmed to operate the temperature control device by means of a pulse width modulation (PWM) of the current. In particular, the incubator may be arranged to operate the temperature control device by means of pulse width modulation (PWM) of the current. The power is then determined in particular by the duty cycle of the PWM, since the amplitude of the current is preferably constant. In particular, the mentioned variables can be variables of the temperature control, i.e. control parameters.

Preferably, an electronic control device of the incubator is configured or programmed so that the temperature control or the control of the incubator gas supply (e.g. $CO_2$, $N_2$, and/or $O_2$), in particular at least one control parameter, can be adapted as a function of the occupancy state of the incubator. In this way, the influence of objects arranged in the interior space of the incubator chamber on the response behavior of the controlled system can be taken into account. In particular, the recovery time can be reduced in the event of a greater occupancy of the interior space.

The data processing device of the object tracking system is preferably separate from a first data processing device of the incubator. However, it may also be part of the control device of the incubator (also referred to as "first control device"), which controls functions of the incubator. In particular, the functions of the control device are implemented by electronic circuits. The data processing device of the object tracking system may comprise at least one CPU, and/or at least one GPU. A GPU may be provided for image processing or performing deep learning processes. Alternatively to a CPU, or a GPU, the data processing device may also comprise a dedicated chip, e.g. the Nvidia Jetson, for image processing or performing Deep Learning processes, which may preferably be used in object tracking, in particular in possible object classification or object individual recognition. Such dedicated chips can be added to the data processing device as computational accelerators. A GPU is already present on many System on a Chip (SoC) systems (for graphics and video rendering). A Raspberry PI can also have a dedicated GPU unit as part of the SOC.

The data storage device preferably comprises at least one data memory, which may in particular be a volatile or a non-volatile data memory. The data acquired or received by the incubator can be stored on this at least one data memory, in particular in at least one database, which can be stored in at least one data memory. Such data includes, in particular, at least one or all of the following types of data: Identification data, ID position data, user identification data, user-related ID position data, object identification data, movement history data, class-related ID position data, individual-related ID position data, occupancy status data, object data, image data, still image data, video image data. The data storage device is preferably a component of the incubator, i.e. in particular arranged in a housing of the incubator. However, it can also be a component of an external data processing device with which the incubator or its data processing device communicates.

The object tracking system may comprise a control device, which may be provided separately from the first control device. The terms "control device" and "control device" are used interchangeably in this description. A control device may include a microprocessor, which may include the data processing device. The microprocessor may be of the "Raspberry Pi" type. The control device and/or the data processing device is preferably configured to perform a control procedure, also referred to as a control software or a control program—each related to the incubator and/or the object tracking system. The functions of the incubator and/or the object tracking system and/or the control device and/or the data processing device can be described in method steps. They can be realized as components of the control program, in particular as subroutines of the control program.

In the context of the present invention, a control device generally comprises or is in particular the data processing device, in particular a computing unit (CPU) for processing data and/or a microprocessor. The data processing device of the control device of the incubator may preferably also be arranged for controlling the object tracking system.

The data processing device of the object tracking system is preferably a device located outside the incubator chamber or incubator and, in particular, optionally separate therefrom, also referred to as an external device or external data processing device. The data processing device and the incubator are preferably in a data connection and are preferably components of a network for data exchange.

The at least one camera of the object tracking system is preferably connected to the control device or data processing device of the object tracking system via a cable connection. For this purpose, the incubator chamber has a through opening through which the cable of the cable connection is guided. Preferably, a seal, in particular a silicone seal, is provided to seal the port in order to prevent (as far as possible) any influence on the atmosphere in the incubator. Alternatively, the camera is connected to the control device or data processing device for wireless data exchange, e.g. via Bluetooth or WLAN.

The incubator may comprise a partial housing in which, in particular, at least one control device (of the incubator and/or of the object tracking system) is arranged. The partial housing is preferably arranged at the rear of the incubator, i.e. in particular opposite the incubator door.

The system, the incubator and/or the object tracking system and/or the data processing device and/or the control device are preferably configured to use the position data of the at least one object or a plurality of objects to form an electronic documentation file in which the movement of the objects is logged and documented. This documentation file is then stored, in particular in a data storage device, and is preferably continuously updated. In this way, "correct" handling of the objects in accordance with standard protocols can be certified as required. On the other hand, deviations from standard protocols can be subsequently identified and/or information correlations can be determined. By collecting such data, the quality of cell-based laboratory work or medical, biological and pharmaceutical procedures can be significantly improved and become more reliable. The reproducibility of cell-based laboratory work can be increased, and deviations from normal characteristics can be detected at an early stage to allow the user to correct or repeat the experiment at an early stage. The documentation file can be provided to the user or an external data processing device by the control device via data exchange. Such documentation is particularly useful in critical applications, e.g., those with a forensic connection or where cells of significant value are cultured.

The incubator is a laboratory incubator and thus a device that can be used to create and maintain controlled climatic conditions for various biological development and growth processes. Preferably, the incubator may be or include a shaker, i.e., an incubator having a movement device for moving objects disposed in the incubator chamber. The incubator may be a cell cultivation device, a microbial incubator (also without $CO_2$). In particular, the incubator is used to create and maintain a microclimate with controlled gas, and/or humidity, and/or temperature conditions in the incubator chamber, and this treatment may be time-dependent. The laboratory incubator, in particular a treatment device of the laboratory incubator, may in particular comprise a timer, in particular a timer, a heating/cooling device and preferably a setting for the regulation of an exchange gas supplied to the incubator chamber, an adjustment device for the composition of the gas in the incubator chamber of the incubator, in particular for adjusting the $CO_2$ and/or the $O_2$ and/or the $N_2$ content of the gas and/or an adjustment device for adjusting the humidity in the incubator chamber of the incubator. The incubator, in particular a treatment device of the incubator, has in particular the incubator chamber, further preferably a control device with at least one control loop, to which the at least one heating/cooling device is assigned as an actuator and at least one temperature measuring device is assigned as a measuring element. By means of the control device, the temperature in the incubator can be controlled. Depending on the embodiment, the humidity can also be controlled via it. A tray filled with water in the incubator chamber can be heated or cooled to adjust the humidity via evaporation. $CO_2$ incubators are used in particular for the cultivation of animal or human cells. Incubators may comprise turning devices for turning the at least one cell culture container and/or a shaking device for shaking or moving the of the at least one cell culture container. The incubator according to the invention is in particular not a bioreactor and/or fermentor.

A sensor device comprises in particular at least one temperature sensor, preferably a plurality of temperature sensors. A temperature sensor can be, for example, a Pt 100 or Pt 1000 temperature sensor. A sensor device preferably has a sensor for determining a relative gas concentration, in particular for determining the content of $CO_2$ and/or $O_2$ and/or $N_2$. A sensor device preferably has a sensor for determining the relative humidity of the air.

An incubator preferably comprises one or a single incubator chamber. This can be divided into compartments. Compartments can be separated by—in particular perforated—bearing plates, whereby in particular a gas exchange between the compartments is made possible. A bearing plate, in particular its lower side, can be configured to hold the camera device and can in particular have a holder for the camera device. A bearing plate, in particular the lower side thereof, can be arranged for holding the illumination device and may in particular comprise a holder for the illumination device.

The incubator chamber comprises chamber walls or chamber inner walls and exactly one or at least one chamber opening via which the objects or cell culture containers can be placed inside the incubator chamber and removed. This chamber opening is closable by a closure element movably connected to the incubator chamber, in particular an incubator door movably mounted on the incubator chamber by means of a hinge, in particular one or more chamber doors. An incubator may have one or more inner doors, which may in particular be transparent, and may have an outer door, which in particular thermally insulates the incubator chamber and optionally at least one inner incubator door, which closes or opens the chamber opening, from the environment. Preferably, images are captured by the image capture system when the incubator door or outer door is closed, so that ambient light does not influence the illumination of the storage area, which is preferably performed exclusively by the illumination device. This leads to particularly well reproducible image recordings that can be easily compared and evaluated by image processing algorithms. Nevertheless, it is also possible for the image recordings to be created with the incubator door open, in particular the outer and/or inner door.

In the closed position of the chamber opening, the interior space of the incubator chamber is preferably insulated from the environment in such a way that a desired atmosphere controlled by the incubator can be set, in particular regulated, in the interior space. In the open position of the chamber opening, gas exchange between the environment of the incubator and the interior space of the incubator chamber is possible via this opening. The chamber opening is typically located in a front wall surrounding the chamber opening.

The incubator chamber preferably comprises a plurality of walls or inner wall surfaces which can be connected to one another, in particular integrally and in particular without edges. The walls or inner wall surfaces are preferably substantially planar in shape, but may also all or in part have a curved shape. The incubator chamber is preferably cuboidal in shape, but may also be otherwise shaped, e.g. spherical, ellipsoidal, polyhedral. The walls or inner wall surfaces are preferably made of a low-corrosion material, in particular stainless steel, copper, brass, or a plastic, in particular a composite plastic. This facilitates cleaning/disinfection of the chamber interior space. Independently of the chamber opening, which serves to load/unload objects or cell culture containers, the incubator chamber can have at least one port for passing an appropriately dimensioned device or cable connection from the interior space of the incubator chamber to its exterior or to the environment of the incubator.

Preferably, the surfaces of the incubator inner walls are configured to be non-glossy or non-reflective, in particular by using a matte surface. The surface of the incubator inner wall can be matted by a surface treatment. The surface treatment may in particular be grinding with an abrasive, which may in particular have a specific grain size. The surface treatment can in particular be irradiation with a blasting medium, in particular sand or glass beads, in particular by compressed air, which can in particular have a specific grain size or a characteristic particle diameter. This can prevent or reduce disturbing reflections in an image.

A typical size of the interior space of an incubator chamber is between 50 and 400 liters.

The incubator may comprise exactly one incubator chamber, but can also have several incubator chambers whose atmosphere (temperature, relative gas concentration, humidity) can be adjustable, in particular individually or collectively. An incubator can have several incubator chambers, each of which can have its own chamber opening and its own chamber door for closing the chamber opening.

The incubator may comprise a housing that partially or completely surrounds the incubator chamber. The housing may be substantially cuboidal in shape, and may in particular be designed such that the incubator is stackable.

A storage area of the incubator is realized in particular by a storage plate, in particular a shelf plate insert and/or a moving platform, which in particular can be made of stainless steel or copper or similar or has this material. A bearing plate serves as a bottom plate, in particular as an intermediate bottom plate. The bearing plate can be removable from the incubator chamber ("bearing plate insert") or can be connected to it in a fixed manner. The incubator chamber may have holding sections or a holding frame for holding one or more bearing plate inserts or insertable instruments.

A bearing plate may be arranged on its underside for holding a camera, in particular have a holder for this camera. Alternatively or additionally, at least one of the inner walls of the incubator chamber may be arranged for holding one or more bearing plate inserts or insertable instruments. For this purpose, a holding structure integrated into the wall may be provided, in particular one or more projections, grooves or webs. A storage plate increases the available storage area in the incubator chamber.

Preferably, substantially all surfaces or at least one surface of the at least one bearing plate are non-glossy or non-reflective, in particular by using a matte surface. The surface of the incubator inner wall may be matted by a surface treatment. The surface treatment may in particular be grinding with an abrasive, which may in particular have a specific grain size. The surface treatment can in particular be irradiation with a blasting medium, in particular sand or glass beads, in particular by compressed air, which can in particular have a specific grain size or a characteristic particle diameter. This can prevent or reduce disturbing reflections in an image.

A holding frame for the at least one bearing plate is also preferably made of a noncorrosive material, preferably stainless steel. The holding frame is preferably designed as a standing object by having at least one base section that rests on the bottom wall of the incubator chamber. However, it may also be supported on the side walls of the incubator chamber and/or suspended from the ceiling wall of the incubator chamber.

A bearing plate preferably—and in particular substantially completely—extends across a horizontal cross-section of the incubator chamber.

Preferably, an incubator has at least two storage plates arranged one above the other. The volume area between two bearing plates, or between a bottom wall of the incubator chamber and a lowermost bearing plate or between a top wall of the incubator chamber and an uppermost bearing plate can be referred to as a storage compartment. A storage compartment may be construed as a whole as a storage area. The surface of a storage plate suitable for storage can be understood as a storage area. The height of a storage compartment is preferably dimensioned such that an object of a certain maximum height (measured perpendicular to the planar surface of a storage plate) or an object stack of objects of a certain maximum height of the stack can be placed on the storage plate. In particular, the maximum height can essentially correspond to the distance between two bearing plates.

The distance between two bearing plates or the maximum height is in particular between 5 cm and 50 cm, preferably between 10 cm and 30 cm, preferably between 10 cm and 20 cm, preferably between 12 cm and 18 cm.

The incubator may have a housing that partially or completely surrounds the incubator chamber. The housing may be substantially cuboidal in shape, and may in particular be designed such that the incubator is stackable.

Preferably, the incubator comprises a treatment device for treating the at least one object, in particular cell culture container. The term "treatment" means in particular that an object, in particular a cell culture or a cell culture container is moved, and/or transported and/or examined and/or changed, in particular physically, chemically, biochemically or in any other way.

A treatment device may be a movement device by means of which the cell medium in at least one cell culture container is kept in motion, preferably via a movement program controlled by the control program. A movement device may be a shaking or pivoting device. A movement device preferably has a support device, in particular a plate, on which one or more cell culture containers are placed and/or fixed. A movement device preferably has a drive device, in particular in the case of a shaking device for example an oscillator drive, in particular in combination with an eccentric, by means of which the desired movement program is implemented. The design of the movement program may depend on the growth stage of the cells of a cell culture and may depend on the cell type, in particular a cell line.

The design and/or control of the treatment, in particular the movement program, may depend on the cell monitoring data. The One treatment device may be a pivoting device by means of which at least one cell culture container is pivoted. The components of the pivoting device may correspond to those of the shaking device, but are set up for a pivoting movement.

A treatment device may also be a transport device by means of which at least one cell culture container can be transported in the incubator chamber. The transport device can be a lift device comprising a carrier device on which the at least one cell culture container can be placed. The lift device preferably comprises a movement mechanism and/or an electrically controllable drive mechanism for driving the movement mechanism. The transport device may further be a movable and electrically controllable gripping arm for gripping and holding at least one cell culture container. The transport device may include a conveyor for moving the at least one cell culture container placed thereon. The transport may move the at least one cell culture container in the incubator chamber, in particular to a processing position in a processing station in the incubator chamber, and away from said processing position. The control means may be arranged to control the transport means in response to cell monitoring data.

The processing station can have at least one measuring device to measure the at least one growth parameter characterizing the growth of the cells of this cell culture. If the at least one cell culture container is movable in the incubator by means of transport equipment, the cell cultures of several cell culture containers can be measured successively with a single or with a few measuring devices. However, several or a plurality of measuring devices can also be provided to observe the growth of several cell cultures in parallel.

The measuring device can also be attached to a transport device. The measuring device can be attached or fastened to a positioning mechanism by means of which the measuring device can be moved and positioned in the incubator chamber. The positioning mechanism may include a movable robotic arm and is preferably electrically controllable, in particular by a control program of the control device. In this way, the growth of the cells of several cell culture vessels can be measured successively with one or with a few measuring devices successively. The positioning mechanism can be designed as a component that can be inserted into the incubator chamber. The power supply of this component may be provided via a cable connection to the incubator, preferably via a power supply connected through a wall opening, e.g. a port, or via such a cable connection to an external power source. The control device may be arranged to control the positioning mechanism in response to cell monitoring data.

The term treatment device can also be understood to mean the temperature control device of the incubator chamber, which is used to control the atmosphere inside the incubator chamber to the desired value, in particular 37° C. The term tempering refers to raising and lowering the temperature of the atmosphere by heating and cooling. Preferably, the temperature inside is adjusted by changing the temperature of the walls of the incubator. Temperature sensors of the corresponding temperature control device are distributed in at least one position inside and/or outside the incubator chamber, in particular on a wall of the incubator chamber.

Preferably, the incubator comprises a user interface device via which the user can input data to the data processing device or the control device, and/or via which information can be output to the user. Preferably, the incubator or said user interface device is arranged to allow the user to input at least one operating parameter for operating the incubator or the object tracking system to or receive information from said user interface device. In this way, a single user interface device can be used by the user to influence, or control, or obtain information from, the incubator and also the at least object tracking system. In particular, the object tracking system can be arranged to display position data or free storage space to the user in response to a user query made by means of the user interface device of the incubator, or to display information derived from position data, (e.g. identity of the user who caused the position change), in particular also statistical information, such as frequency and time of the position change of an object (a sample) and/or—e.g. percentage—available free storage space and/or at least one optical image of the at least one object. This is advantageous for the user, since he receives essential information based on this information, which, on the one hand, allows him to plan experiments more precisely—before he carries out an experiment he knows that storage space is available; on the other hand, the change in position of samples, in particular in the first hours after the seeding of adherent cells, negatively influences their adherence; no uniform cell lawn is then formed. Providing the information on position changes or their frequency according to the invention allows the user to determine causes of non-uniform cell growth and thus to take them into account in future experiments.

An equipment-controlled treatment of the incubator is preferably a program-controlled treatment, i.e., a treatment controlled by a program. By a program-controlled treatment of a sample it is to be understood that the process of treatment is essentially carried out by executing a plurality or a plurality of program steps. Preferably, the program-controlled treatment is performed using at least one program parameter, in particular at least one program parameter selected by a user. A parameter selected by a user is also referred to as a user parameter. Preferably, the program-controlled treatment is performed by means of the digital data processing device, which is in particular part of the control device. The data processing device may comprise at least one processor, i.e. a CPU, and/or comprise at least one microprocessor. Preferably, the program-controlled treatment is controlled and/or carried out according to the instructions of a program, in particular a control program. In particular, in a program-controlled treatment, substantially no user action is required at least after the program parameters required by the user have been acquired. Device-controlled treatment of the incubator can be carried out in particular as a function of the end position and/or the user-related ID position data.

A program parameter is a variable which can be set in a predetermined manner within a program or subprogram, valid for at least one execution (call) of the program or subprogram. The program parameter is set, e.g. by the user, and controls the program or subprogram and causes a data output depending on this program parameter. In particular, the program parameter and/or the data output by the program influences and/or controls the control of the device, in particular the control of the treatment by means of the at least one treatment device.

A program is understood to mean in particular a computer program. A program is a sequence of instructions, in particular consisting of declarations and instructions, in order to be able to process and/or solve a specific functionality, task or problem on a digital data processing device. A program is usually present as software to be used with a data processing device. In particular, the program may be present as firmware, in particular in the case of the present invention as firmware of the control device of the incubator or the system. The program is usually present on a data carrier as an executable program file, often in so-called machine code, which is loaded into the main memory of the computer of the data processing device for execution. The program is processed as a sequence of machine, i.e. processor, instructions by the processor(s) of the computer and is thus executed. By 'computer program' is understood in particular also the source code of the program, from which the executable code can arise in the course of the control of the laboratory device.

A user interface device may be a component of an incubator, or a module. A user interface device preferably has in each case: a control device for the user interface device; a communication device for establishing a data connection with a laboratory device, in particular an incubator, via an interface device thereof; an input device for detecting user inputs from a user; an output device, in particular a display and/or a display, for outputting information to the user, in particular a touch-sensitive display. In this context, the control device of the user interface device is preferably configured to exchange data with the control device of the incubator via the data connection.

The object placed in the incubator and tracked by object tracking may be, in particular, a cell culture container, or another laboratory sample holder, e.g., a slide, or may be another laboratory object, e.g., a device, in particular, a rocking shaker, a shaker, a pH meter.

An object is in particular a cell culture container. A cell culture container is in particular transparent. In particular, it is made of glass or plastic, in particular PE or PS, and in particular has a planar base plate which forms the growth surface of the cells. This may have a surface treatment to promote cell adherence. The cell culture container can be closed or provided with a PE cap or gas exchange cap, in particular a lid with optionally included filter. In particular, the cell culture container is stackable. An Eppendorf cell culture bottle is particularly suitable. The object can be a stack of cell culture containers, in particular a stack of Petri dishes or of cell culture bottles.

The camera of the object tracking system can have wide-angle optics, in particular fisheye optics, whose image angle in the image diagonal can be between 160° and 180°. Preferably, one camera—or several cameras—is mounted on the underside of a shelf insert in the incubator chamber, or on an underside of the upper inner wall of the incubator chamber, preferably in each case vertically above the geometric center etc. of the storage area that the camera monitors. However, one or more cameras may also be arranged/mounted on inner side walls of the incubator chamber. "Bottom" refers to the direction of gravity, "top" to the opposite direction. In intended use, incubators are arranged so that the tops of the planar shelf inserts are horizontal. In particular, the incubator camera is suitable to operate reliably in the particular incubator atmosphere for a period of several months or years, or to operate reliably during the lifetime measured under standard conditions (room temperature). Not every camera is suitable to operate in an incubator atmosphere. One possible commercially available camera is the 5MP Wide Angle Camera for Raspberry Pi, www.joy-it.net, available from Conrad Electronic SE, Germany, and/or another camera in combination with a wide angle lens, e.g. commercially available the "Industrial lens HAL 250 2.3", Entaniya Co., Ltd., Japan. Alternatively, a cover device may be provided for the at least one camera to shield or isolate it from the incubator atmosphere, said cover device in particular having transparent regions or a transparent window or being transparent to allow image capture through the transparent regions.

Preferably, the data processing device is programmed to detect from one or more still images, and/or the start image, and/or the end image, and/or from the video data (time-dependent) changes in the appearance (or appearance) of the objects, in particular between longer time intervals of minutes, hours or days. In this way, color changes of the cell culture medium or colors in a cell culture container or structures, e.g. droplets, on a cell culture container wall can be determined. Such colors, color changes or structures may indicate problems of the respective cell culture, e.g. nutrient deficiency, pH change and/or mold, and/or other contaminations. Preferably, the data processing device is programmed to output information to the user or operating personnel via a user interface depending on the detection of the appearance of a cell culture container and/or these changes in the appearance of the cell culture container and/or to store the data about this detection (in particular: what was detected and when) in a data memory.

Preferably, the data processing device is programmed to determine from one or more still images, and/or the start image, and/or the end image, and/or from the video data (time-dependent) changes in the appearance of the objects, in particular between longer time intervals of minutes, hours or days.

In particular, the invention also relates to a system for incubating live cell cultures, comprising
 an incubator for incubating live cell cultures, which comprises:
an incubator chamber for receiving objects, in particular cell culture containers, in at least one storage area of the incubator chamber, which has a closable chamber opening for loading and unloading the objects,
a data processing device and a data memory,
 an image-processing object tracking system configured to retrofit the incubator for tracking position changes of at least one object introduced into the incubator chamber starting from its start position in a start image of a storage area to its end position in an end image of the storage area, the object tracking system comprising
 comprises at least one data processing device, a data memory, and at least one camera adapted to monitor an interior space of the incubator chamber,
 wherein the data processing device is programmed to,
assign identification data to the at least one object introduced into the interior space, determine the start position of the at least one object from the start image of the storage area and the position changes of the at least one object by evaluating the video data,
determine the final position of the at least one object in the final image of the storage area from the position changes, and store the end position of the at least one object in the storage area in dependence on the identification data as ID position data in the data memory in a retrievable manner.

The foregoing system is thus based on an incubator that is retrofittable with a retrofittable object tracking system, such as is an integral part of the incubator in claim 1, wherein the retrofittable object tracking system must be correspondingly compatible with the "compatible incubator" so designated.

Preferably, a control device of the incubator according to the invention or of the compatible incubator, which in particular can also control the atmospheric parameters in the incubator chamber (temperature, gas partial pressure $CO_2$, $H_2O$ etc.), or its data processing device is configured or programmed to determine at least one operating parameter of the incubator as a function of data from the object tracking system, in particular position data or the end position of at least one object, in particular a parameter which controls the display of information on a screen of the incubator or a parameter which is displayed on the screen of the incubator. In particular, position data or the final position of at least one object can be displayed on the screen.

Preferably, the system for incubating live cell cultures comprises: an external device separate from the incubator and in data exchange connection with the latter, in particular a user identification device, in particular a mobile user identification device, and in particular a data exchange device by means of which the data processing device can exchange data with the external device, in particular can determine user identification data by means of the user identification device.

The invention also relates to a method of tracking object placements in an incubator used to incubate live cell cultures in an incubator chamber of the incubator, comprising the computer controlled steps:
  monitor the incubator chamber by means of at least one camera of the incubator arranged to record at least one storage area in the interior space of the incubator chamber into which the at least one object is placed;
  assign identification data to the at least one object captured in a start image of the storage area taken by means of the at least one camera as it is brought into the interior space;
  detect of position changes of the at least one object by evaluation of video data obtained by means of the camera; in particular, the simultaneous movement of several objects, in particular inventory objects, is enabled or executed;
  determine the final position of the at least one object in a final image of the storage area from the position changes;
  store the end position of the at least one object in the storage area as a function of the identification data as ID position data, in the data memory, in particular retrievable storage, i.e. storing and making available the respective data, in order to enable access by a data processing device and reading of the data.

In the process, preferably exactly one object (can also be a stack or group of objects) is introduced into the interior space and its end position is determined. It is also possible and preferred that in the process it is registered that during the setting of the one object at least one inventory object is moved, for example by being pushed by means of the one inserted object, and thus the end position of the at least one inventory object is determined from its position changes determined by image processing. It is also possible and preferred that in the method several objects are introduced into the interior space, simultaneously and/or successively, and that these objects are each assigned an identification number from a start image, their position changes are determined from video data, and from this their end position in a final image is determined in each case.

Preferably, the method comprises the step of: Reading in user identification data identifying the user of the incubator who introduces the at least one object into the incubator chamber by means of a user identification device, and in particular storing the user identification data in a data memory of the incubator.

Preferably, the method comprises the step of: store the position data of the at least one object in dependence on the user identification data as user-related object position data.

The invention also relates to an image-processing object tracking system, in particular configured to retrofit an incubator, for tracking changes in position of at least one object introduced into the incubator chamber, starting from its starting position in a starting image of a storage area to its final position in a final image of the storage area, wherein the object tracking system,
  comprises at least one data processing device, a data memory, and at least one camera adapted to monitor an interior space of the incubator chamber,
  wherein the data processing device is programmed to,
assign identification data to the at least one object introduced into the interior space,
determine the start position of the at least one object from the start image of the storage area and the position changes of the at least one object by evaluating the video data,
determine the final position of the at least one object in the final image of the storage area from the position changes, and
store the end position of the at least one object in the storage area in dependence on the identification data as ID position data in the data memory.

Further preferred embodiments of the method according to the invention can be obtained from the description of the incubator according to the invention and its preferred embodiments. Furthermore, further embodiment options of the invention result from the embodiment examples in the figures. Identical components of the embodiments are identified by substantially the same reference signs, unless otherwise described or otherwise apparent from the context. Showing:

FIG. 3 shows a front view of the incubator from FIG. 1 with a graphic representation of the occupancy of the incubator chamber with objects that are highlighted in a user-specific color-coded manner.

FIG. 4a shows a smartphone with camera and display 63 as an external device that can be part of a system 400 comprising the incubator 1 of FIG. 3 and the smartphone 69.

FIG. 4b shows a legend of the color coding used in the screen of FIG. 3 to highlight user-related objects.

Figure 5A:
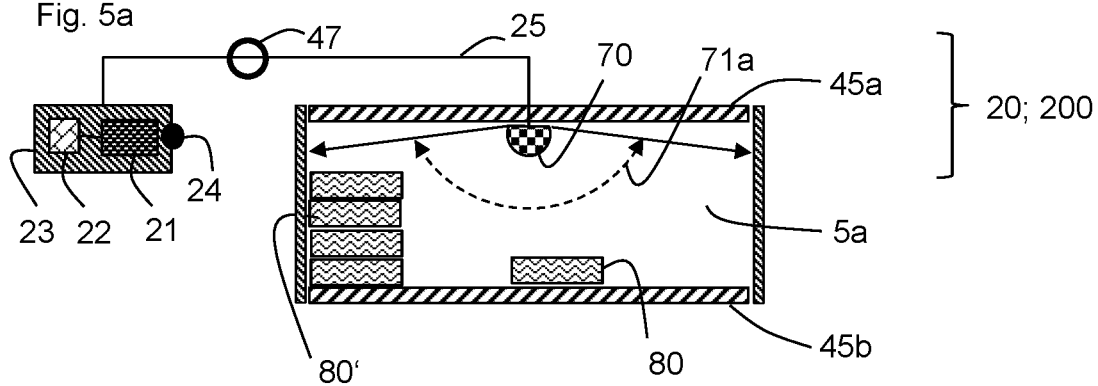

FIG. 5a shows a schematic side view of an object tracking system as part of the incubator of FIGS. 1 to 4b in an example of a chamber with a single monitored bearing plate.

Figure 5B:
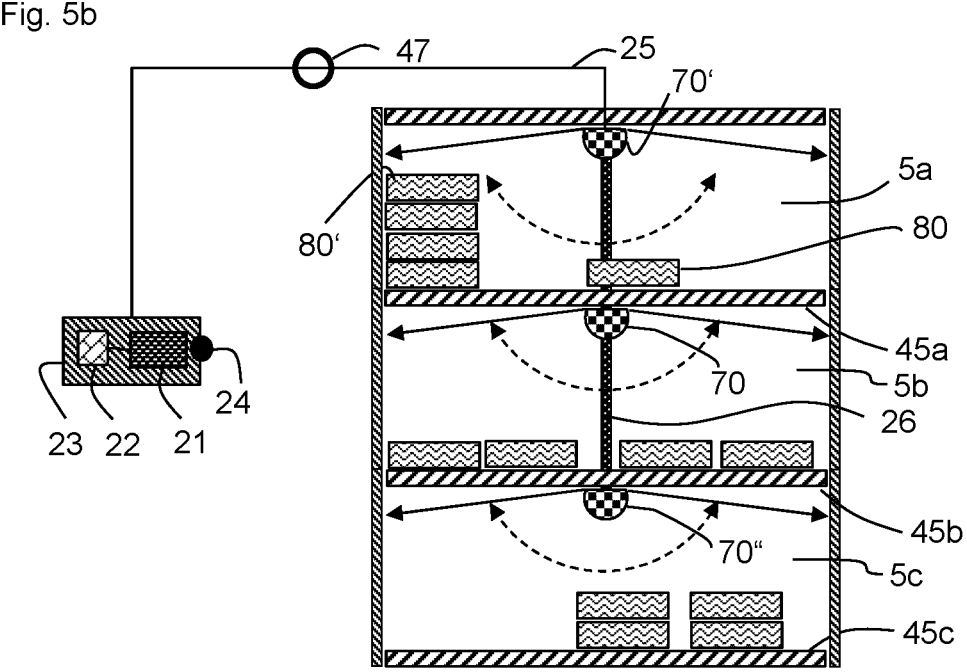

FIG. 5b shows a schematic side view of an object tracking system as part of the incubator of FIGS. 1 to 4b in an example of a chamber with multiple monitored bearing plates.

Figure 5C:
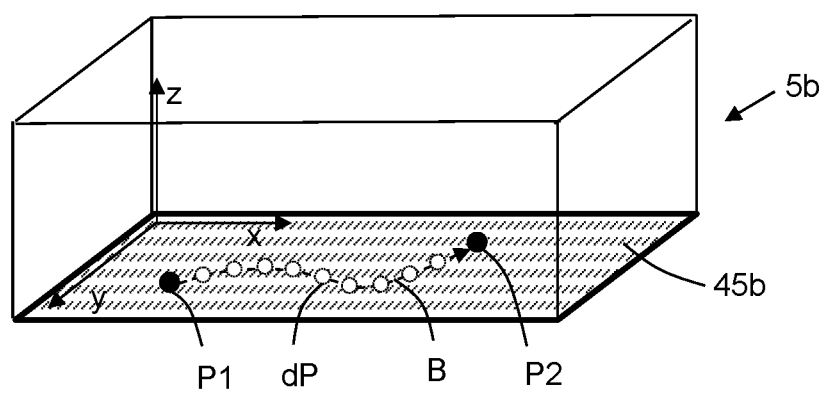

FIG. 5c shows a perspective view of a storage area monitored by the object tracking system of FIGS. 5a and 5b, and the start position P1, position changes dP, and end position P2 of a tracked object relative to a coordinate system.

Figure 5D:
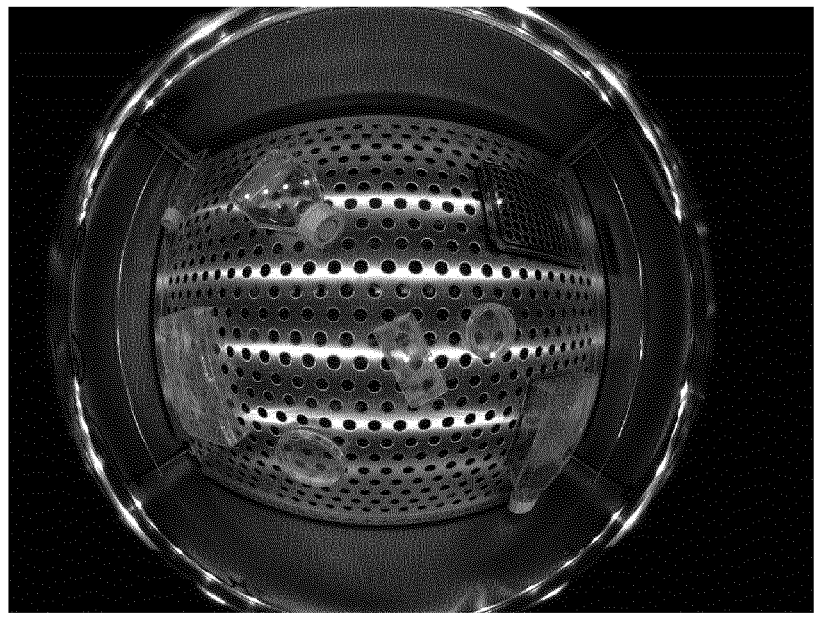
Figure 5D:
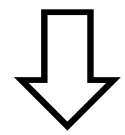

FIG. 5d shows a digital image captured by the wide-angle fisheye camera of the object tracking system used in FIGS. 5a and 5b, which appears distorted due to the optics.

Figure 5E:
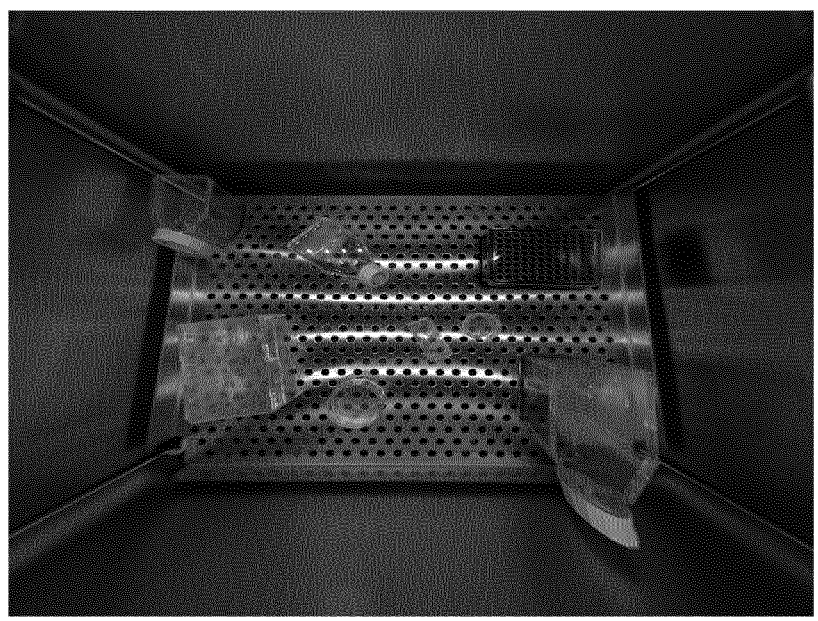

FIG. 5e shows the image of FIG. 5d rectified by the object tracking system using straightening algorithms.

Figure 5F:
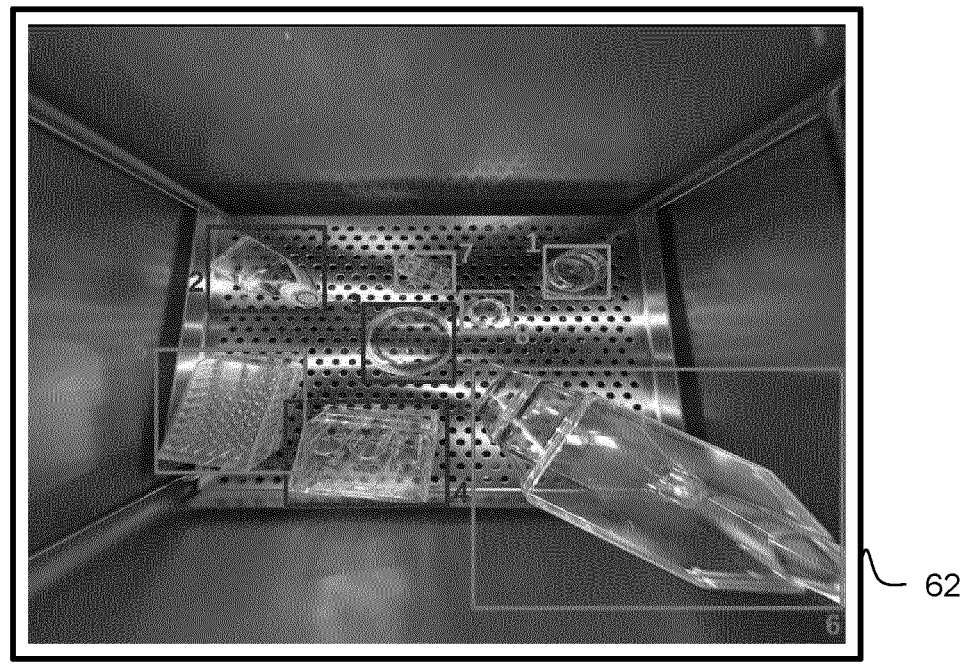

FIG. 5f shows a still image captured by the wide-angle fish-eye camera of the object tracking system used in FIGS. 5a and 5b for output to a screen of the incubator, showing the bounding boxes of the object tracking system, identification numbers, and color coding identifying the user/owner.

Figure 5G:
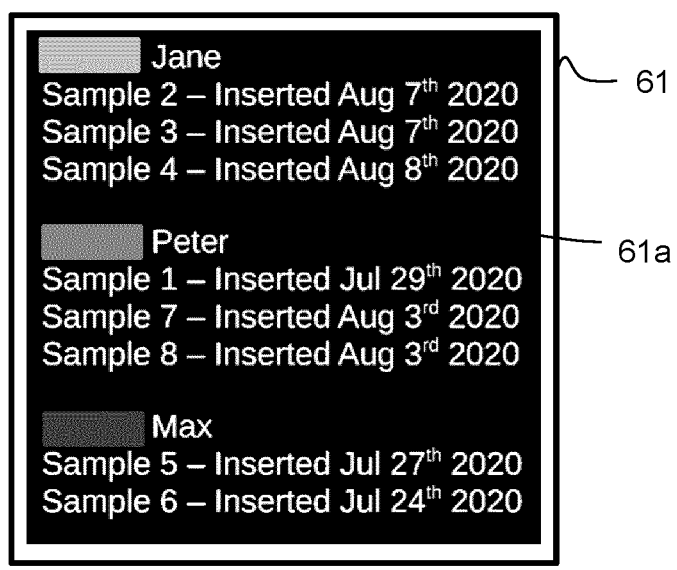

FIG. 5g shows possible screen content that can be displayed on a screen of the incubator to explain the screen shown in FIG. 5f.

Figure 6:
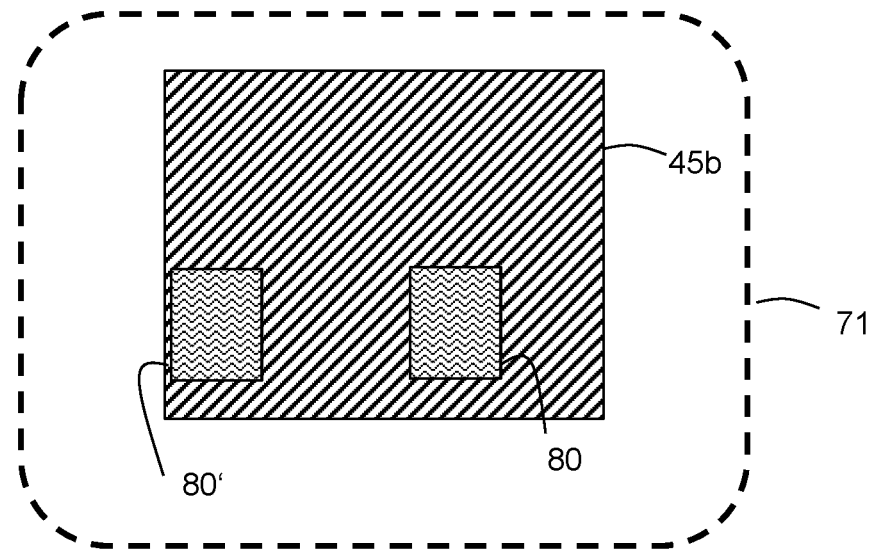

FIG. 6 shows a schematic top view of a storage area of the incubator of FIGS. 1 to 5, including objects, arranged in an image capture section of a camera of the object tracking system.

Figure 7:
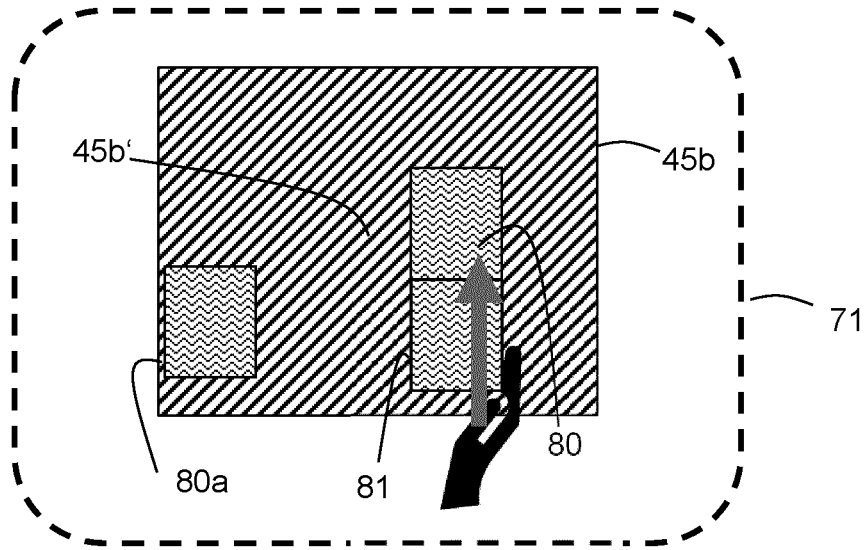

FIG. 7 shows the displacement of a stock object by a new object moved into the incubator using the section from FIG. 6.

Figure 8E:
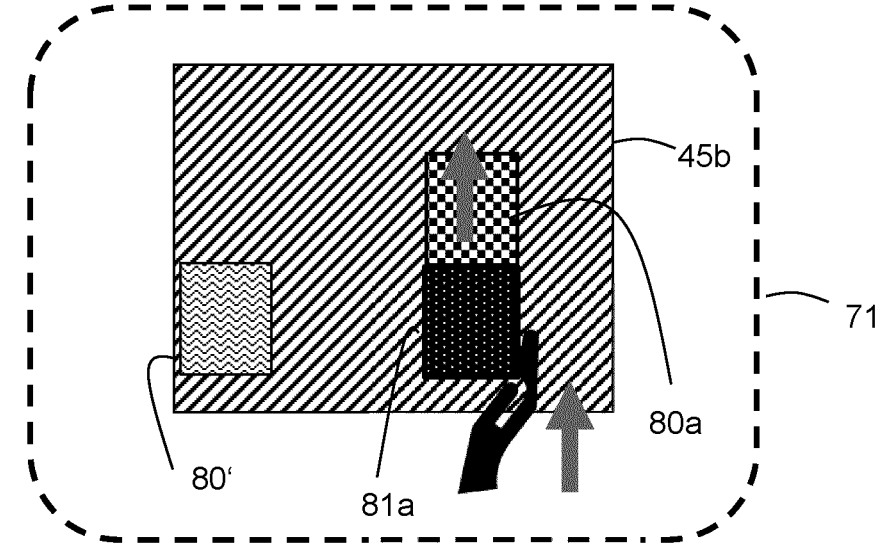
Figure 8F:
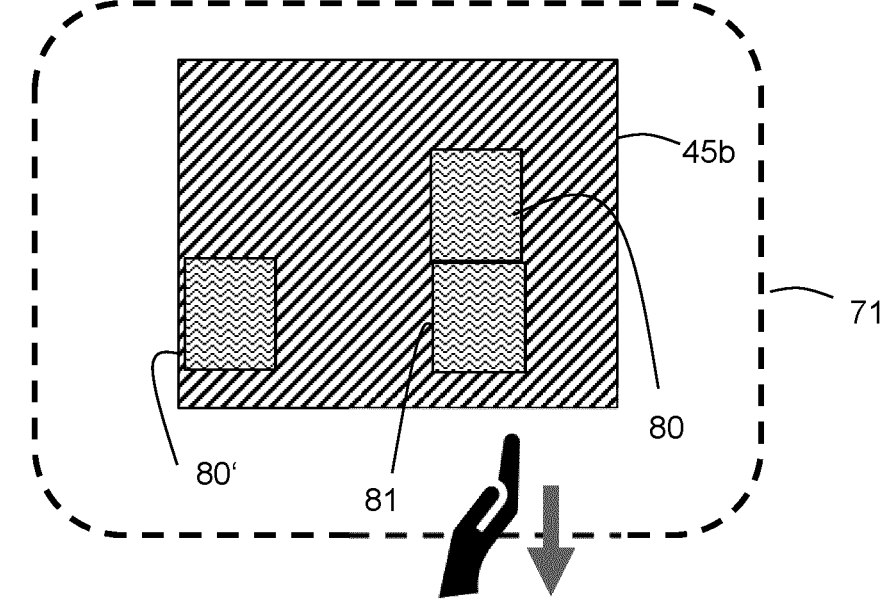

FIGS. 8a to 8f each show a different phase of motion of the objects in the section of FIG. 6, with definition of the bounding box of the moving objects by algorithms of the object tracking system. FIG. 8a shows the start image, and FIG. 8f shows the end image.

Figure 9:
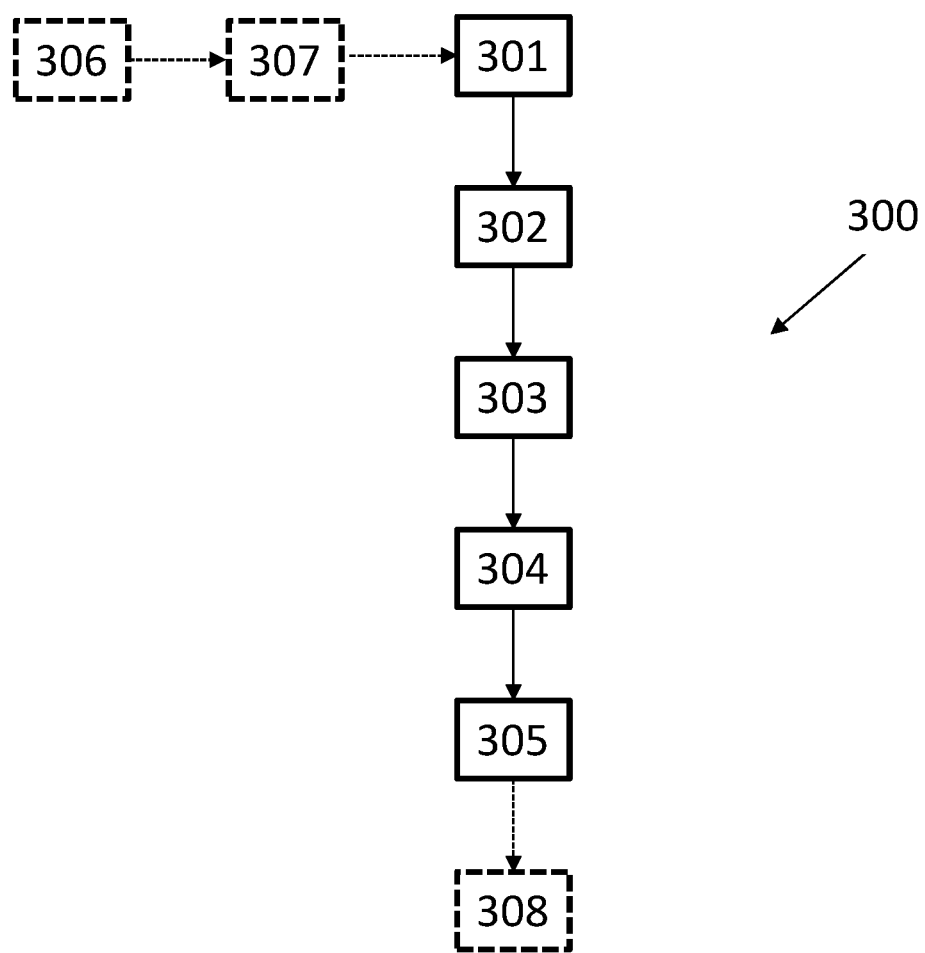

FIG. 9 schematically shows the sequence of an exemplary process according to the invention.

FIG. 1a shows an incubator 1 for storing laboratory samples, more specifically a $CO_2$ incubator for storing live cell cultures in a defined atmosphere at a controlled temperature, e.g. 37° C. For this purpose, the chamber interior space 5 of the incubator is thermally insulated and can be sealed gas-tight from the environment, and the gas composition in the interior space is also controlled and can be changed via gas connections 43. The chamber housing 2 of the incubator stands on pedestals 44, encapsulates the interior space 5 and opens into the front side 3 of the incubator. The front face has the chamber opening 4 through which the chamber interior space 5 is accessible. A transparent inner chamber door 6 serves to close the chamber opening in a closed position of the chamber door. In the incubator 1, the chamber housing 2 is placed within the interior space of an outer housing 40 so that the chamber housing 2 and the outer housing 40 are spaced apart and thermally insulated from each other. Shelf plate inserts 45 and a humidifier tray 46 are visible in the chamber interior space. The front side 3 of the chamber housing and the front side of the outer housing coincide in the present case.

The outer incubator door 41 and the chamber door 6 are shown in an open position. The outer door 41 is hinged to the outer edge of the outer housing and has a circumferential silicone seal 42.

When the outer door 41 has been opened, the inner chamber door 6 of the incubator is initially still closed. The closing device (10, 7a, 7b) is used for this purpose. With the chamber door 6 closed, the user can first view the interior space 5 through the transparent door wall before opening the door and inserting or removing a laboratory sample. Nevertheless, opening the outer incubator door 41 already represents a disturbance that can potentially damage the incubator atmosphere.

The incubator has an external camera 65 built into the door 41 and facing forwards, the images of which can be analyzed by the suitably programmed data processing device of the incubator, in particular to identify a user by means of facial recognition, whereby the external camera 65 connected to the data processing device serves as a user identification device 66. The latter can also be done via the camera of the smartphone 69.

In the incubator, in order to protect the stored laboratory samples, it is effective to minimize the time during which the interior space of the incubator is exposed to the environment (opening time intervals). The present invention is based on the observation that the opening time intervals can be reduced by an object tracking system. The incubator 1 has an object tracking system (not shown in FIGS. 1, 2).

Figures 1, 2:
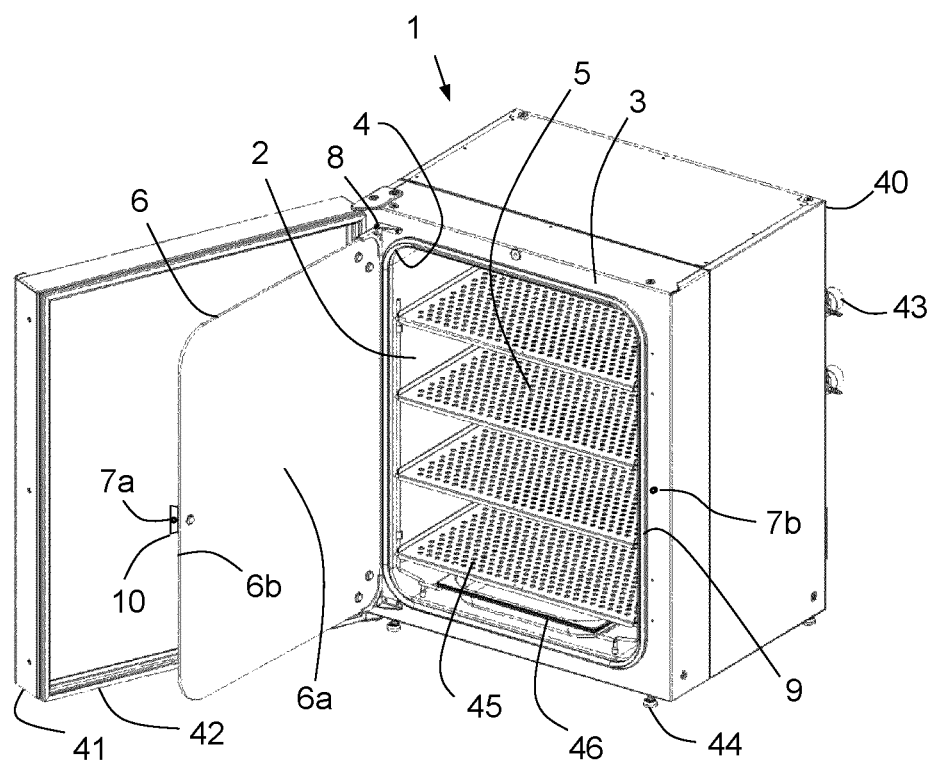
FIG. 1 shows a perspective view of an incubator according to an embodiment of the invention.
FIG. 2 shows a front view of the incubator from FIG. 1.

As shown in FIG. 2, the outside of the outer incubator door has a first screen, a touch screen 61, via which operating parameters of the incubator 1 are displayed, e.g. the temperature of the incubator atmosphere or a gas partial pressure in the interior space 5.

The exterior of the outer incubator door 41 includes a second screen 62, which may be a touch screen. The data processing device (not shown) of the incubator 1 is programmed to display on the screen 62 the occupancy of the interior space of the incubator. The screen 62 serves as a "digital window" that allows the user to (virtually) view the interior space of the incubator. The graphical display of the interior space of the incubator and its occupancy by inventory objects can be programmed in such a way that certain inventory objects are graphically highlighted depending on certain criteria or condition parameters.

Re FIG. 3: The data processing device of the incubator 1 is programmed to display one or more objects in the display 62 as a function of at least one condition parameter, which here depends on user identification data, in accordance with their respective end position in the interior space of the incubator determined by means of the object tracking system. In each case, the inventory objects associated with particular user identification data identifying with a particular user are highlighted with a particular user-dependent color The legend 61a for this type of color coding is shown to the user here via the upper display 61 in the sub-area 61a thereof. Legend 61a is shown larger in FIG. 4b: the user identifiers "Jane", Joe", etc. are associated with the corresponding highlighting colors used in display 62, 63.

In FIG. 4, it is shown that the output display 61 and/or 62 can also—alternatively or additionally—be component(s) of an external device, here a smartphone 69, which is in a data exchange connection with the incubator and has the display 63, which functions here as a component of an incubator system.

FIG. 5a shows a schematic front view of shelf inserts 45a and 45b of the incubator 1, which are arranged one above the other. The vertical distance of such shelf inserts 45 in incubators is usually not large and is, for example, between 10 and 40 cm, in the case of incubator 1 about 15 cm. This means that either several cameras must be used to cover the entire storage area, in this case the entire storage area of the shelf insert 45b and the "air space" above it up to the shelf insert 45a. The camera 70 is a wide-angle fisheye camera with an angle of view of approximately 180°.

FIG. 5a shows the object tracking system 20 installed in the incubator 1, which is also designated by the reference sign 200 in the case of the retrofit system embodiment. The object tracking system 20 includes the camera 70, a wide-angle fisheye camera that captures the storage area of the shelf sheet insert 45b below it at a viewing angle 71a of preferably 160° to 170°. The wide angle of view makes it possible to use a single camera to capture the entire storage area of the bottom shelf insert 45b, in particular also the air space into which the (inventory) objects 80' and 80 protrude, namely a stack 80' of cell culture containers and a cell culture container 80. The nominal angle of view of the wide-angle fish-eye camera is even 200°, but only an image area is evaluated which corresponds to an angle of view taken from the range of preferably 160° to 170°.

The camera is arranged vertically above the geometric center of the storage surface of the shelf sheet insert 45*b*. The object tracking system 20 also includes the control device 23, which includes a data processing device 21 and a data memory 22 as further components of the object tracking system 20. The data processing device 21 and the control device 23, respectively, are connected to the camera 70 and the other three cameras not shown, each of which is provided so that all storage areas (all upper sides of shelf sheet inserts 45, see FIG. 1) are monitored, via a cable connection 25 that enters the incubator chamber through the port 47 in the incubator chamber rear wall. The control device 23 also includes a data interface 24 for enabling a data connection to other incubator device components, for example, to output data or signals to a display 61, 62, 63 of the incubator.

FIG. 5*b* shows a schematic side view of an object tracking system as part of the incubator from FIGS. 1 to 4*b* in an example of a chamber with several monitored bearing plates. The illustration is an extension of the principle of FIG. 5*a*, in which the incubator chamber is divided into several compartments 5*a*, 5*b* and 5*c*, which are here arranged one above the other and are connected for gas exchange, which is formed via holes in the bearing plates 45*a*, 45*b*, 45*c*. The bearing area or bearing plate 45*a* in compartment 5*a* is monitored by camera 70', the bearing area or bearing plate 45*b* in compartment 5*b* is monitored by camera 70', and the bearing area or bearing plate 45*c* in compartment 5*c* is monitored by camera 70", the cameras 70' and 70" being designed and arranged analogously to camera 70 in FIG. 5*a*. All cameras are connected to the control device 23 via a connection cable bundle 26 inside the incubator chamber, which merges into the cable connection 25 already shown in FIG. 5*a* and leaves the incubator chamber through port 47 in the incubator chamber rear wall, the data processing device 21 of which is configured to monitor all objects in all three compartments 5*a*, 5*b* and 5*c*. Here, the object tracking system of the incubator belonging to FIG. 5*b* comprises three cameras 70, 70', 70" the data processing device 21 and the data storage device 22.

FIG. 5*c* shows a perspective view of a compartment 5*b* or storage area 45*b* monitored by the object tracking system of FIGS. 5*a* and 5*b*, as well as the start position P1, position changes dP, and end position P2 of an object tracked on its motion path B with respect to a Cartesian coordinate system (x, y, z). The origin of the coordinate system can be fixedly located in a corner of the compartment.

FIG. 5*d* shows a digital image captured by the wide-angle fisheye camera of the object tracking system used in FIGS. 5*a* and 5*b*, which appears distorted due to the optics.

FIG. 5*e* shows the image of FIG. 5*d* rectified by the object tracking system using straightening algorithms.

FIG. 5*f* shows a still image captured by the wide-angle fish-eye camera of the object tracking system used in FIGS. 5*a* and 5*b* for output to a screen of the incubator, showing the bounding boxes of the object tracking system, identification numbers, and color coding identifying the user/owner.

FIG. 5*g* shows possible screen content that can be displayed on a screen of the incubator to explain the screen shown in FIG. 5*f*. In addition to identifying the objects by identification numbers, color coding identifying the user/owner is also shown, as well as the times of placing the objects in the incubator chamber as recorded by the object tracking system.

FIG. 6 shows a storage area, namely the upper side of the shelf plate insert 45*b*, from a bird's eye view or in top view. Also shown schematically is the image capture section 71 captured by the camera 70. The image capture section 71 is the area captured by the camera 70 in one or each frame, because the camera 70 does not change its angle of view or position. Thus, each still image, the start image, the frames that can be extracted from the video data, and the end image shows this image capture section 71. In the figures, the lower edge of the image capture section 71 represents the area located near the incubator chamber opening 4.

FIG. 7 shows how a user (shown: his hand) places a cell culture container 81 in the incubator, or more precisely, moves it forward or inside the incubator on the storage area 45*b'*. In doing so, he also moves the stock object 80, which is externally indistinguishable from the object 81. If the new object 81 arrives in its final position exactly at the previous position of the stock object 80, it will not be possible to distinguish between the object 80 and the object 81 from still images created before the adjustment and after the adjustment of the new object 81. However, this is possible by means of the object tracking system 20, 200, as explained with reference to FIGS. 8*a* to 8*e*.

The data processing device of the object tracking system 20, 200 is programmed to acquire and evaluate the video data by means of the camera 70 with the detection of the door opening of the outer door 41 of the incubator. By comparing successive frames of the video data in time, it can be determined when a new object enters the camera section 71. An image containing an outline 81*a* newly appearing in the cutout 71, which can be assigned to the object 81 introduced into the interior space, is regarded as a start image. Such an image results from the situation in FIG. 8*a*. Based on this start image, identification data and a bounding box are assigned to the newly appeared outline 81*a*, assuming that it is a new object 81 to be placed in the incubator. The object tracking algorithms of the object tracking system 20, 200 track the object defined by the bounding box through the now subsequent frames of video data. From these frames, the changes in position of the object 80 are determined by analyzing the video data. Ignoring initially the fact that the user pushes the stock object 80 deeper into the incubator chamber by means of the new object 81, starting from its original position (its previously detected end position), the following now happens with respect to the tracking of the new object 81:

In FIG. 8*b*, the entire object is recognizable as an outline 81*a*, and the user's hand itself could also initially be understood by the data processing system 21 as part of the object 81, but this is corrected at the latest when the hand is removed. It is understood by the object tracking system that the moving, and image components associated with the outline 81*a* are initially parts of the object 81. This outline 81*a* is defined by a bounding box to reduce the computational effort of tracking, and is continuously tracked through the frames (FIG. 8*a* to FIG. 8*e*) and position changes of the outline (bounding box) 81*a* are detected, so that the current position of the bounding box 81*a* can be taken from each frame. If no more movement of the bounding box 81*a* is detected, the frame is taken as the "end frame" of the object movement (so in FIG. 8*e*) and the end position of the new object 81 is calculated from the end frame and the end position of the object 81 in the storage area is stored in the data memory as ID position data depending on the identification data of the at least one object.

As a complication, in the process shown in FIGS. 8a to 8e, the movement of the new object 81 displaces the stock object 80 from its previous position and the new object even occupies the exact previous position of the stock object 80. However, even in this situation, the object tracking system 20, 200 allows the objects 80 and 81 to remain uniquely distinguishable. The object tracking system 20, 200 is configured and programmed to simultaneously track a plurality of objects and their position changes, and thus their final positions after a movement:

The data processing device 21 is programmed to
assign identification data to the at least one object 80 (the inventory object) introduced into the interior space—this step was already performed when the inventory object 80 had been introduced into the incubator chamber as a "new object 80" at an earlier time;
determine the start position of the object 80 (inventory object) from the start image of the storage area and the position changes of the object 80 (inventory object) by evaluating the video data. In particular, the start image is a still image that was created before the object 81 was set, or an image determined from the video data;
track the object 80 (inventory object) by determining the changes in position of the object 80 between its start position and end position;
determine in the final image the (new) final position of the object 80 in the storage area; and
store the end position of the object 80 (inventory object) in the storage area as ID position data in the data memory 22 in dependence on the identification data of the object 80.

FIG. 9 shows the sequence of the process according to the invention, which was also indirectly mentioned in the above description of FIGS. 8a to 8f.

The method 300 for tracking object positioning in an incubator 1 used for incubating live cell cultures in an incubator chamber 2, 5 of the incubator, comprising the computer controlled steps:
monitor the incubator chamber 2, 5 by means of at least one camera of the incubator arranged to record at least one storage area 45b' in the interior space of the incubator chamber into which the at least one object 80; 81 is placed; (301)
assign identification data to the at least one object 80; 81 captured in a start image of the storage area taken by means of the at least one camera when or after it is brought into the interior space; (302)
detect changes in position of the at least one object 80; 81 between its start position and end position by evaluating video data obtained by means of the camera 70; in particular, detecting simultaneous changes in position of several objects or inventory objects; (303)
determine the final position of the at least one object 80; 81 in a final image of the storage area; (304)
store the final position of the at least one object 80; 81 in the storage area in dependence on the identification data of the at least one object as ID position data, in the data memory; (305)
Preferably, the method 300 also includes the steps of:
in particular before steps 301 to 305, 308: reading in user identification data identifying the user of the incubator 1 who introduces the at least one object 80; 81 into the incubator chamber by means of a user identification device (306), and storing the user identification data in a data memory of the incubator; (307)

Preferably, the method 300 also includes the step of:
Store the ID position data as a function of the user identification data as user-related ID position data; (308).

The invention claimed is:

1. An incubator for incubating live cell cultures, comprising
an incubator chamber for receiving objects, in particular cell culture containers, which comprises a closable chamber opening for loading and unloading the objects and at least one storage area for storing the objects,
an image-based object tracking system for tracking position changes of at least one object introduced into the incubator chamber starting from its start position in a start image of a storage area to its end position in an end image of the storage area by means of video data, wherein the object tracking system,
at least one data processing device, a data memory and at least one camera, which is arranged to monitor an interior space of the incubator chamber and to provide the start image, the end image and the video data,
wherein the data processing device is programmed to,
assign identification data to the at least one object introduced into the interior space,
determine the start position of the at least one object from the start image of the storage area;
determine the position changes of the at least one object between the start position and an end position by evaluating the video data,
determine the final position of the at least one object in the final image of the storage area, and
store the final position of the at least one object in the storage area as a function of the identification data of the at least one object as ID position data in the data memory.

2. The incubator according to claim 1, comprising a user identification device by means of which a user using the incubator is identifiable in terms of user identification data.

3. The incubator according to claim 2, wherein said data processing device is programmed to
identify a user using the incubator by means of the user identification device and assign user identification data to him, and
store ID position data in dependence on the user identification data as user-related ID position data in the data memory.

4. The incubator according to claim 2, wherein the user identification device comprises an outdoor camera, and the user identification device is adapted to perform a facial recognition by means of the outdoor camera, by means of which the user is identified.

5. The incubator according to claim 2, wherein the user identification device comprises a user interface device by means of which user identity data is readable, in particular selectable, or comprises a reader for reading a code identifying the user, wherein the reader is in particular an RFID reader, a barcode reader, or a QR code reader.

6. The incubator according to claim 1, comprising:
an incubator door for closing the chamber opening and
a door sensor for detecting the opening or closing of the incubator door,
wherein the data processing device is programmed to
start the monitoring of the interior space of the incubator, in particular the generation of the video data or of still image data, depending on the detection of a door opening of the incubator, in particular in dependence on the detection of a door opening by a user, to identify this user by means of a user identification device, in particular to terminate the monitoring of the interior space of the incubator, in particular the generation of the video data, depending on the detection of a door closure of the incubator, in particular by means of the information to determine from the user identification device and the object tracking device, by which user which object was moved in the interior space, and to store the user identification data of this user together with the object identification data of this object in the data memory.

7. The incubator according to claim 1, wherein the data processing device is programmed to determine the movement history, in particular the movement path, of the at least one object within the incubator chamber from the start image, the video data and/or the end image and to store it in the form of movement history data in the data memory.

8. The incubator according to claim 1, comprising an object recognition system configured to take object class features of the at least one object from the start image, the video data, and/or the end image, match the object class features with an object class database and recognize the object class of the at least one object, assign the recognized object class as object class data to the ID position data of the at least one object and storing it as class-related ID position data; or configured to take object individual characteristics of the at least one object from the start image, the video data, and/or the end image, match the object individual characteristics with an object individual database and if the object individual characteristics in the object individual database are associated with an object individual identifier: identify the object individual identifier of the at least one object; or if the object individual characteristics in the object individual database are not associated with an object individual identifier: assign an object individual identifier to the at least one object and store it in the object individual database; and assign the recognized individual object identifier to the ID position data of the at least one object and storing it as individual-related ID position data.

9. The incubator according to claim 1, comprising a display screen, wherein the data processing device is programmed to display a graphical representation of the interior space of the incubator chamber on the display screen, and in particular to graphically display where the object identified by the ID position data is located, or to graphically display where all objects located in the interior space are located.

10. The incubator according to claim 9, wherein the data processing device is programmed to determine, based on predetermined user identification data, where the objects associated with said predetermined user identification data by means of the user-related ID position data are positioned and, in particular, to mark said objects graphically on the screen.

11. The incubator according to claim 9, wherein the data processing device is programmed to display on the screen free storage space, and/or information derived from the position data, in particular the identity of the user who brought about the position change, and/or statistical information, in particular the frequency and time of the position change of an object and/or the percentage of free storage space available.

12. A system for incubation of live cell cultures, comprising an incubator for incubating live cell cultures, comprising:
an incubator chamber for receiving objects, in particular cell culture containers, in at least one storage area of the incubator chamber, which has a closable chamber opening for loading and unloading the objects, a data processing device and a data memory, an image-processing object tracking system configured to retrofit the incubator for tracking position changes of at least one object introduced into the incubator chamber starting from its start position in a start image of a storage area to its end position in an end image of the storage area by means of video data, wherein the object tracking system comprises at least one data processing device, a data memory and at least one camera, which is arranged to monitor an interior space of the incubator chamber and to provide the start image, the end image and the video data, wherein the data processing device is programmed to
assign identification data to the at least one object introduced into the interior space;
determine the start position of the at least one object from the start image of the storage area,
determine the position changes of the at least one object between the start position and an end position by evaluating the video data,
determine the final position of the at least one object in the final image of the storage area, and
store the end position of the at least one object in the storage area in dependence on the identification data of the at least one object as ID position data in the data memory.

13. The system according to claim 12, comprising
a user identification device usable separately from the incubator, and a data exchange device by means of which the data processing device can determine user identification data based on the user identification device.

14. A method for tracking object placements in an incubator used to incubate live cell cultures in an incubator chamber of the incubator, comprising the computer-controlled steps of:

monitor the incubator chamber by means of at least one camera of the incubator arranged to record at least one storage area in the interior space of the incubator chamber and to generate the start image, the end image and video data into which the at least one object is placed;

assign identification data to the at least one object captured in a start image of the storage area taken by means of the at least one camera when or after it is brought into the interior space;

detect position changes of the at least one object between the start position and an end position by evaluating video data obtained by means of the camera;

determine the final position of the at least one object in a final image of the storage area;

store the end position of the at least one object in the storage area as a function of the identification data of the at least one object as ID position data, in the data memory.

15. The method according to claim 14, comprising the step of:
    read in user identification data identifying the user of the incubator who introduces the at least one object into the incubator chamber by means of a user identification device, and storing the user identification data in a data memory of the incubator.

16. The method according to claim 14, comprising the step of:
    save the ID position data depending on the user identification data as user-related ID position data.

17. The method according to claim 14, comprising the step of: visualize the stored ID position data and/or the user-related ID position data on the screen, in particular by graphically displaying the interior space of the incubator chamber on the screen, and in particular graphically displaying the information where the object identified by the ID position data is positioned, or where all objects located in the interior space are located, or displaying the free storage space in the interior space of the incubator on the screen.

* * * * *